(12) United States Patent  (10) Patent No.: US 7,927,034 B2
Staniforth et al. (45) Date of Patent: Apr. 19, 2011

(54) APPLICATION DEVICE FOR TOPICAL ADMINISTRATION OF PHARMACEUTICAL COMPOSITIONS AND PRODUCTS

(75) Inventors: John Staniforth, Bath (GB); Michael Tobyn, Wiltshire (GB); Sharon Ann Mills, Bath (GB); Christopher John Althorpe, Cardiff (GB)

(73) Assignee: Pharmakodex Limited, Hippenham, Wiltshire (GB)

( * ) Notice: Subject to any disclaimer, the term of this patent is extended or adjusted under 35 U.S.C. 154(b) by 0 days.

(21) Appl. No.: 10/431,360

(22) Filed: May 6, 2003

(65) Prior Publication Data

US 2004/0071494 A1      Apr. 15, 2004

Related U.S. Application Data

(60) Provisional application No. 60/380,030, filed on May 6, 2002, provisional application No. 60/409,264, filed on Sep. 9, 2002.

(51) Int. Cl.
  *B43K 23/12*         (2006.01)
(52) U.S. Cl. .......................................... 401/262; 401/88
(58) Field of Classification Search .................... 401/88, 401/98, 261, 262, 132, 49, 118, 119, 266; 424/400, 401, 408, 448, 449, 489, 65; 4/49, 4/88, 130, 266
  See application file for complete search history.

(56) References Cited

U.S. PATENT DOCUMENTS

| 1,888,314 | A | * | 11/1932 | Framke | 132/317 |
| 2,179,735 | A | * | 11/1939 | Beem | 401/196 |
| 2,557,141 | A | * | 6/1951 | Rebora | 132/294 |
| 2,606,565 | A | * | 8/1952 | Sage, Sr. | 132/320 |
| 3,299,464 | A | * | 1/1967 | O'Brien et al. | 15/104.94 |
| 3,871,390 | A | * | 3/1975 | Spatz | 132/293 |
| 4,014,616 | A |   | 3/1977 | Mast, Jr. et al. | 401/292 |
| 4,090,642 | A |   | 5/1978 | Baker | |
| 4,101,053 | A |   | 7/1978 | Mast | |
| 4,151,274 | A |   | 4/1979 | Schlueter et al. | 424/80 |
| 4,235,557 | A | * | 11/1980 | Hayes | 401/49 |
| 4,369,784 | A |   | 1/1983 | de Buman et al. | 128/271 |
| 4,519,795 | A | * | 5/1985 | Hitchcock et al. | 604/289 |
| 4,699,161 | A |   | 10/1987 | Smith et al. | 132/73.5 |
| 4,701,168 | A | * | 10/1987 | Gammons | 604/310 |
| 4,728,210 | A | * | 3/1988 | Barish et al. | 401/6 |
| 4,765,986 | A |   | 8/1988 | Liedtke | 424/449 |
| 4,848,378 | A | * | 7/1989 | Moir et al. | 132/319 |
| 4,884,680 | A | * | 12/1989 | Israel et al. | 206/457 |
| 4,892,890 | A |   | 1/1990 | Damani | 514/784 |
| 4,893,956 | A | * | 1/1990 | Wojcik et al. | 401/130 |
| 4,963,045 | A | * | 10/1990 | Willcox | 401/132 |

(Continued)

FOREIGN PATENT DOCUMENTS

DE          3523454 A1      1/1987

(Continued)

*Primary Examiner* — Huyen Le
(74) *Attorney, Agent, or Firm* — Davidson, Davidson & Kappel, LLC

(57) ABSTRACT

An applicator for applying a spreadable composition to the skin or other exterior region of a human or animal body, comprising receiving means for receiving and carrying a unit or measured dose of the composition and a grip for enabling a user to grip and manipulate the applicator, wherein the grip and receiving means are arranged such that a user gripping the applicator by the grip is protected from inadvertent contact with a composition, a unit or measured dose of which is carried by the receiving means.

57 Claims, 18 Drawing Sheets

U.S. PATENT DOCUMENTS

| | | | | |
|---|---|---|---|---|
| 4,994,049 | A | * | 2/1991 | Latzke et al. ............... 604/307 |
| 5,230,119 | A | | 7/1993 | Woods et al. ............... 15/209.1 |
| 5,308,343 | A | | 5/1994 | Gafner ......................... 604/289 |
| 5,368,581 | A | * | 11/1994 | Smith et al. ................. 604/290 |
| 5,504,962 | A | | 4/1996 | Byun ............................. 15/184 |
| 5,597,849 | A | | 1/1997 | McGinity et al. ............ 514/648 |
| 5,646,109 | A | * | 7/1997 | Owen et al. ..................... 514/2 |
| 5,771,524 | A | * | 6/1998 | Woods et al. ............... 15/209.1 |
| 5,863,941 | A | | 1/1999 | Liedtke ........................ 514/555 |
| 5,879,769 | A | * | 3/1999 | Greenland et al. ........... 428/35.7 |
| 5,881,743 | A | | 3/1999 | Nadel .......................... 132/320 |
| 5,904,151 | A | | 5/1999 | Gueret ......................... 132/293 |
| 6,250,049 | B1 | * | 6/2001 | Feldman et al. ............... 53/452 |
| 6,312,181 | B1 | * | 11/2001 | Joulia .......................... 401/196 |
| 6,467,981 | B1 | | 10/2002 | Gueret ......................... 401/201 |
| 6,493,898 | B1 | * | 12/2002 | Woods et al. ............... 15/209.1 |

FOREIGN PATENT DOCUMENTS

| | | |
|---|---|---|
| EP | 0375763 B1 | 12/1989 |
| EP | 0376852 B1 | 7/1990 |
| EP | 0839472 | 5/2002 |
| FR | 2780622 | 7/1998 |
| WO | 9119222 A1 | 12/1991 |
| WO | 0200203 A1 | 1/2002 |

* cited by examiner

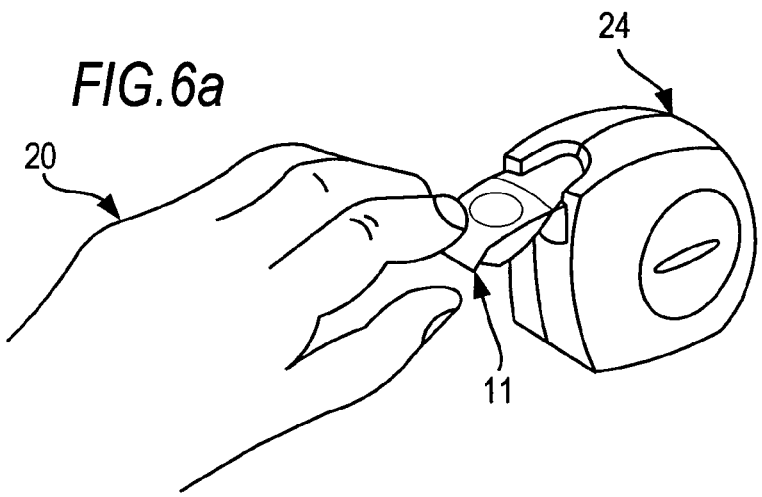
FIG.6a
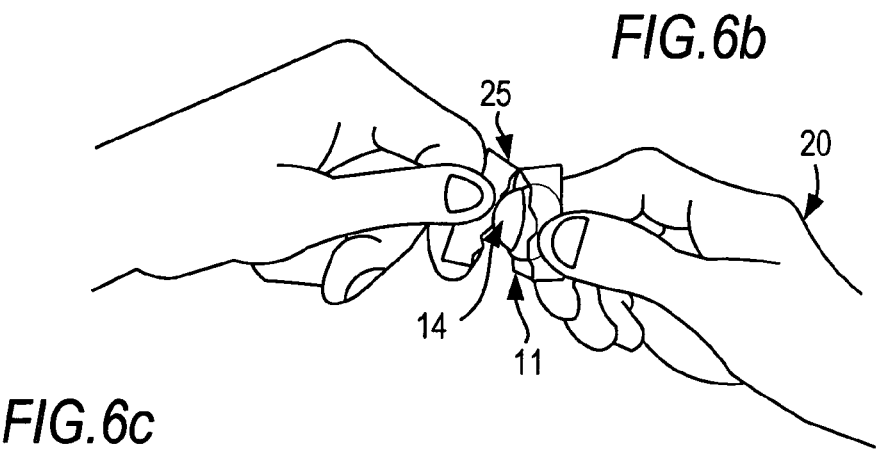
FIG.6b
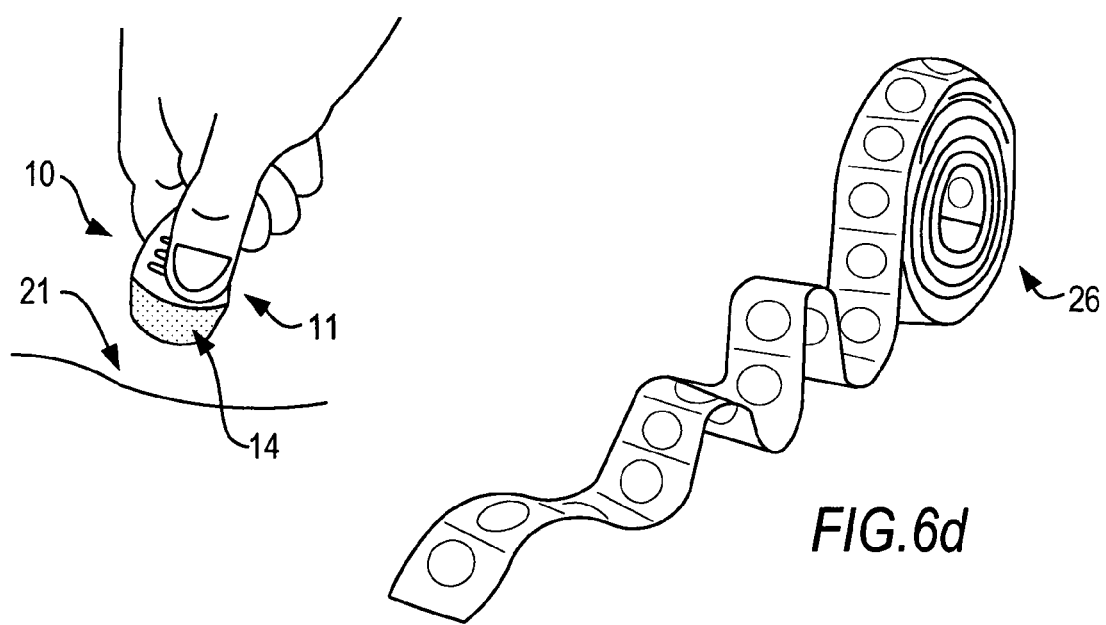
FIG.6c
FIG.6d

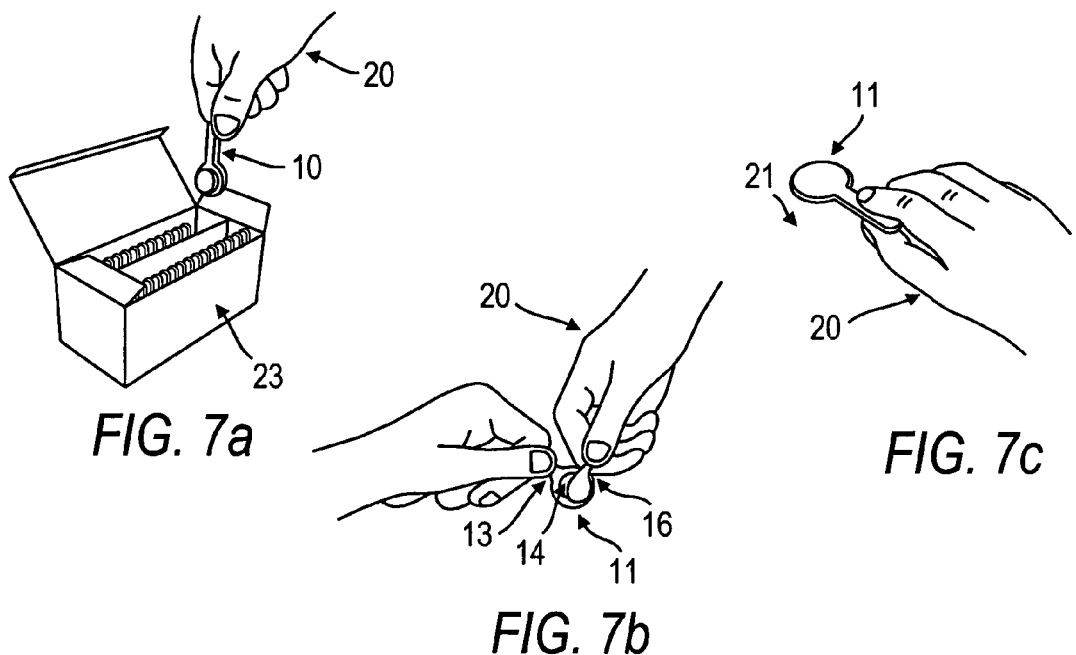
FIG. 7a
FIG. 7b
FIG. 7c
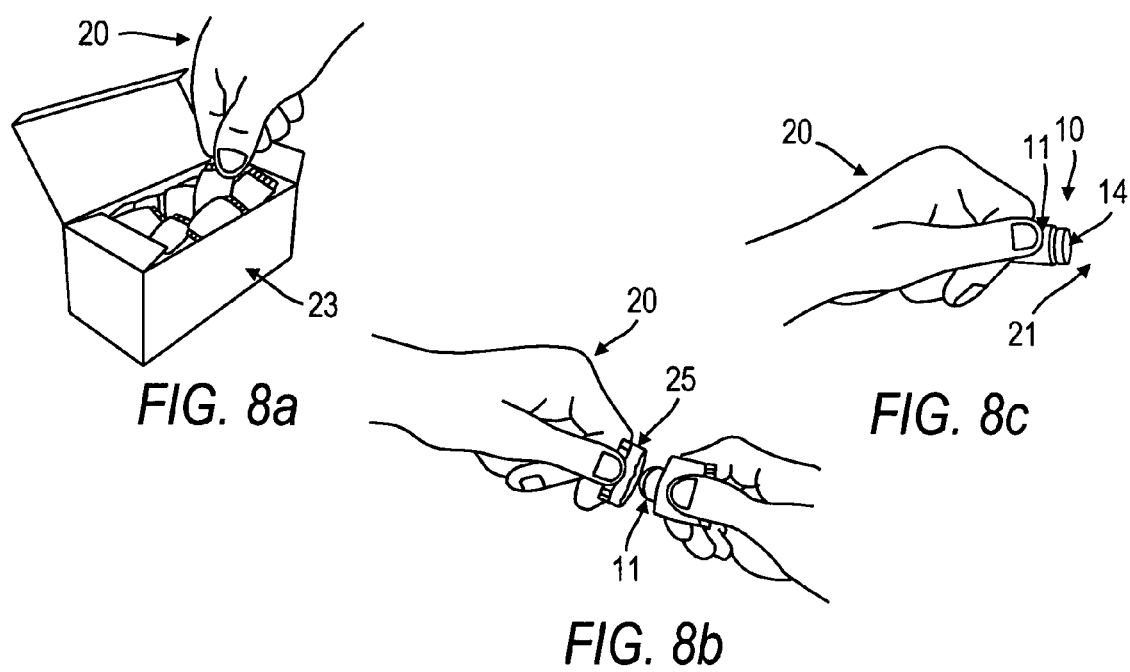
FIG. 8a
FIG. 8b
FIG. 8c

APPLICATION DEVICE FOR TOPICAL ADMINISTRATION OF PHARMACEUTICAL COMPOSITIONS AND PRODUCTS

This application claims priority from U.S. Provisional Application Ser. No. 60/380,030 filed May 6, 2002 and U.S. Provisional Application Ser. No. 60/409,264, filed on Sep. 9, 2002, the disclosures of which are incorporated by reference in their entirety.

DESCRIPTION

The present invention relates to applicator devices for administering spreadable compositions, preferably pharmaceutical compositions, formulations and products containing therapeutic agents, to the skin and/or other external regions of preferably living human or animal bodies.

The present invention is related to the subject matter disclosed in WO 02/002 03 A1, the entire disclosure of which is hereby incorporated by reference.

In the treatment of localised disorders, such as skin infections or the like, it is often desirable to prescribe therapeutic agents in forms that have a topical, or localised effect. Topical formulations are available in a variety of forms, including creams, ointments, solutions, lotions, suspensions, pastes, emulsions, foams and the like. Water miscible creams are generally employed for moist or weeping lesions, whereas ointments are generally chosen for dry, lichenified or scaly lesions, or where a more occlusive effect is required. Lotions are often used when minimal application to a large or hair-bearing area is required or for the treatment of exudative lesions.

It is important with any dosing regime for it to be adhered to accurately. In the case of topical formulations, a higher than appropriate dose can easily be applied by accident, and it is particularly important, therefore, that patients using such formulations follow their dosing instructions carefully to avoid any adverse effects.

In addition, it is important when applying some topical formulations, that only the affected skin area is contacted by the drug. This is particularly important for cases in which the drug is toxic, for example drugs used in treating warts. Thus, a system for dermal administration of pharmaceutical formulations should enable the user to apply the pharmaceutical formulation to a desired skin region without contacting any skin region outside the desired skin region. This would include, for example, the patient's fingers, or the skin of a caregiver, such as a nurse.

Hitherto, the quantities of topical formulations prescribed for specific areas of the body have been as follows:

|  | Creams and Ointments (g) | Lotions (mL) |
| --- | --- | --- |
| Face | 15 to 30 | 100 |
| Both Hands | 25 to 50 | 200 |
| Scalp | 50 to 100 | 200 |
| Both Arms or Both Legs | 100 to 200 | 200 |
| Trunk | 400 | 500 |
| Groins and Genitalia | 15 to 25 | 100 |

In most cases, the above amounts have been prescribed to adults for twice daily application for one week. However, the above recommendations are not applicable for all topical formulations and a number of categories of topical formulation require specialised dosing regimes. For example, the above recommendations are not applicable to corticosteroid preparations. More particularly, for potent corticosteroid formulations, more care is required as absorption through the skin can cause severe pituitary-adrenal-axis suppression and Cushing's syndrome, both of which depend on the area of the body treated and the duration of the treatment. Corticosteroid preparations, therefore, have normally been applied once or twice daily (it has not been found necessary to apply them more frequently) and the quantities hitherto prescribed (to adults for twice daily application for one week) for specific areas of the body have been as follows:

|  | Creams and Ointments (g) |
| --- | --- |
| Face and Neck | 15 to 30 |
| Both Hands | 15 to 30 |
| Scalp | 15 to 30 |
| Both Arms | 30 to 60 |
| Both Legs | 100 |
| Trunk | 100 |
| Groins and Genitalia | 15 to 30 |

Furthermore, the treatment of severe atopic eczema on the limbs or body (or a flare-up of mild to moderate eczema) has often required still further consideration. For example, treatment has in some cases required application of a potent or moderately potent corticosteroid for the first one to two weeks, followed by a weaker preparation as the condition improves; an emollient has also been used.

It will be appreciated from the foregoing that considerable care is required in following a dosing regime for topical formulations and a particular consideration that should be taken into account is the maximum dosage that can be tolerated for any therapeutic agent during a treatment course. For example, the following are specific examples of prior art topical formulations where specific dosing regimes, and in particular maximum dosages, have been instructed.

Doxepin Hydrochloride is supplied as a 5% preparation. The recommended maximum dose of this preparation is 3 g applied thinly three to four times daily to an area of less than about 10% of the body surface, with no more than 12 g of the preparation to be applied per day.

Clobetasol Propionate is recommended to be applied thinly one or two times daily for up to four weeks, typically with a maximum administration of about 50 g of a 0.05% preparation per week.

Diflucortolone Valerate is recommended to be applied one or two times daily for up to four (0.1% preparation) or two (0.3% preparation) weeks, with typically a maximum administration of about 60 g of a 0.3% preparation per week.

It has been observed that it is especially important for the maximum dosage of topical formulations of Calcipotriol to be monitored. For example, there has been seen to be a risk of hypercalcaemia if the recommended maximum weekly dose of Calcipotriol is exceeded. In this regard, the recommended dosing regime for a topical formulation of Calcipotriol has been to apply once or twice daily, with a maximum weekly dose of 100 g. For patients over six years, the formulation should be applied twice daily; for patients from six to twelve years, a maximum weekly dose of 50 g; and for patients over twelve years, a maximum weekly dose of 75 g. Unfortunately, the above has not always been clearly explained in the patient information provided with topical formulations of Calcipotriol. For example, the information provided with the topical formulation of Calcipotriol available under the trade mark Dovonex® advises liberal application, despite the above described potential for hypercalcaemia.

A major cause of patients failing to comply with appropriate treatment regimes for the administration of therapeutic agents to the skin, is that they find it difficult to measure out precise amounts of conventional topical formulations. This has made it especially difficult to ensure that patients receive an accurate dosing of therapeutic agent. One method of metering the amount of a therapeutic agent to be applied to a patient's skin via a topical formulation, that has been employed in the past, is to instruct the patient to squeeze the topical formulation from a dispenser, such as a tube, along an index finger starting at the fingertip down to the first joint. The amount of therapeutic agent thus measured has become known as one fingertip unit (FTU) and patients can be instructed to apply multiples or fractions thereof. One FTU approximates to about 500 mg of a topical formulation and is generally sufficient to cover an area that is twice that of a flat adult hand. Such administration has not, however, hitherto achieved accurate dosing because the FTU is only an approximate unit and its magnitude varies from patient to patient. Another disadvantage is that the pharmaceutical formulation comes into contact with the skin of the index finger during such administration, which may not be desirable in many instances.

It has also been known to deliver therapeutic agents transdermally by applying to the skin of a patient an adhesive patch containing a therapeutic agent. Such patches typically have further included a rate-moderating membrane, an adhesive, a liner and a backing material. The adhesive has often required special formulation to ensure compatibility with the other components of such patches and this type of formulation has often increased the cost of such patches. Furthermore, not all therapeutic agents are suitable for inclusion in such patches. For example, therapeutic agents having a localised therapeutic effect have not hitherto been effectively employed in such patches.

Such patches have also been referred to in the pharmaceutical field as "medicinal plasters". For example, U.S. Pat. No. 4,765,986 describes a medicinal plaster which comprises a drug present in a carrier substance and the carrier substance is affixed to a porous and flexible synthetic material.

U.S. Pat. No. 5,863,941 is also concerned with dermal administration of therapeutic agents and in particular describes a method of treating pathological symptoms of the inner ear. More particularly, U.S. Pat. No. 5,863,941 describes the use of a carrier substance and a therapeutic agent, the latter comprising a local anaesthetic present in an amount of about 0.5 to 40% by weight of the carrier substance. The carrier substance and therapeutic agent described in U.S. Pat. No. 5,863,941 for use in the treatment of the inner ear, may take the form described in U.S. Pat. No. 4,765,986.

EP 0 375 763 B describes an applicator device for dosing a liquid, such as medicinal solution, onto the skin of a patient. The device described by EP 0 375 763 B includes a micrometric screw dosing mechanism which allows variation of the internal cavity thereof. An applicator device of the type described in EP 0 375 763 B, however, is only suitable for use with therapeutic agents that can be provided in solution.

To alleviate problems encountered with treatment regimes where it is important to observe a maximum dosage of a therapeutic agent for dermal administration, it would be beneficial to be able to provide means for substantially accurately dermally administering such a therapeutic agent to a patient. Such accurate administration should obviate the detrimental side effects that have hitherto been observed when maximum dosages have been exceeded.

In addition, it would be beneficial for such means for dermal administration of a therapeutic agent to enable a user to administer the therapeutic agent to a desired skin region without the therapeutic agent contacting a skin region outside the desired skin region, for example the patient's fingers, or the skin of a caregiver, such as a nurse. A caregiver who had to treat several patients with a toxic drug would otherwise be exposed to large amounts of the drug.

In accordance with the present invention there is provided an applicator for applying a spreadable composition to the skin or other exterior region of a human or animal body, comprising receiving means for receiving and carrying a unit or measured dose of the composition and a grip for enabling a user to grip and manipulate the applicator, wherein the grip and receiving means are arranged such that a user gripping the applicator by the grip is protected from inadvertent contact with a composition, a unit or measured dose of which is carried by the receiving means.

In embodiments, the applicator is shaped to shield the grip, or a zone in the vicinity of the grip from contact with a composition, a unit or measured dose of which is carried by the receiving means. Such shielding can be achieved by the provision of a shroud around at least a portion of the grip, or a zone in the vicinity of the grip. Preferably, the grip is arranged to be held between a finger and thumb of a user's hand and the applicator can be shaped to shroud the tips of a finger and thumb holding the grip. Alternatively, the grip can be in the form of a sheath arranged to engage and accommodate a user's finger or thumb.

It is preferred that the receiving means forms a portion of a spreading means for facilitating the spreading of the composition on the skin or other exterior region of a human or animal body. The receiving and spreading means can be integrally formed. In embodiments, a combined spreading and receiving means also serves to shield the grip, or a zone in the vicinity of the grip from contact with a composition, a unit or measured dose of which is carried by the receiving means.

In further embodiments, the applicator is a single piece moulding. The grip is preferably foldable or collapsible from a position where is it extended for use into a storage position. It is preferred, when the grip is collapsible, for the applicator to be provided with means for releasably retaining the grip in said storage position.

In a particularly preferred embodiment of the present invention, the applicator's receiving means are arranged to define a recess that can accommodate a unit dose of the spreadable composition with a face of the unit dose exposed for application to the skin and at least a portion of the unit dose within the recess, wherein the depth of the recess adjusts automatically and sufficiently to allow substantially all of a unit dose accommodated in the recess to be applied through skin contact induced erosion at said exposed face of the unit dose. Preferably, the recess is configured to confine at least an uneroded portion of the unit dose and, thus, to provide resistance to the bodily displacement of the latter from the recess. More preferably, the recess is configured to resist displacement of said uneroded portion of the unit dose from the recess other than as a result of skin contact induced erosion at said exposed face of the unit dose.

An advantage of these embodiments of the invention is that, by confining the composition and preventing it from spreading out excessively and possibly being lost from the applicator, a more accurate dosing of the composition can be achieved and the possibility of undesirable contact with the composition can be minimised.

Preferably, a first recess defining portion of the receiving means is resiliently mounted with respect to a second recess defining portion of the receiving means to provide the aforementioned automatic depth adjustment. The first and second recess defining portions of the receiving means can form a platform, a first portion of which is recessable relative to a second to provide said recess. The first portion of the platform can be surrounded by the second portion of the platform. Preferably, the first portion of the platform is variably recessable relative to the second, and the first and/or second portion(s) of the platform can be resiliently mounted. In an embodiment, the first recess defining portion of the receiving means is embodied by the second portion of the platform and the second recess defining portion of the receiving means is embodied by the first portion of the platform. In an alternative embodiment, the first recess defining portion of the receiving means is embodied by the first portion of the platform and the second recess defining portion of the receiving means is embodied by the second portion of the platform.

Preferably, the first portion of the platform comprises a pad in a fixed relationship with the grip, said pad being surrounded by the second portion of the platform, and said second portion of the platform is retractable relative to the pad and grip against resilient pressure.

It is preferred for the grip, or a zone in the vicinity of the grip, to be protected or shielded from contact with the spreadable composition during application of the latter.

As set out in the foregoing passages, applicators in accordance with the invention are for use in applying a spreadable composition to the skin or other exterior region of a human or animal body. In certain preferred embodiments, applicators in accordance with the invention include a unit or measured dose of such a composition carried on or coupled to their receiving means.

Preferably, the unit or measured dose of the spreadable composition is, at ambient or room temperatures, a solid unit dosage form and, more preferably, a solid tablet. In embodiments, the receiving means comprises a surface adapted to retain such a solid unit dosage form or tablet. In this last regard, the surface of the receiving means can be roughened, or can include one or more raised portions capable of penetrating at least part-way into a solid unit dosage form, such as a tablet.

The spreadable composition is preferably solid at ambient or room temperatures, but softens sufficiently to be spreadable on contact with the skin of a live human or animal body, i.e., when raised to a physiological temperature. The temperature at which a composition softens sufficiently to be spreadable is defined as its "softening point". Preferably, the softening point of a composition is the temperature at which, on heating the composition, its viscosity is reduced to 100,000 and preferably 50,000 centipoise, or below. Alternatively, the softening point of a composition can be determined using a TA-XT2 texture analyser using the following protocol. The analyser should be equipped with a 5 kg load cell and enclosed in a temperature controlled chamber (capable of operating in the region of –60° C. to 200° C.). The unit dosage form to be measured should then be enclosed in the chamber at a specified temperature for a time of at least 10 minutes. A 3 mm flat faced probe is then pushed into the unit dosage form for a distance of 1 mm at a speed of 0.1 mm/sec. Measurement should then be repeated at temperature increments of 1° C. and the temperature at which the peak force of resistance recorded (as measured by Texture Exceed Software) falls below 50% of that for the dosage form when solid is deemed to be its softening point.

Preferably, the solid compositions and unit dosage forms employed with applicators in accordance with the invention remain solid or substantially solid when heated up to a temperature of 25, 26, 27, or 28° C., but soften sufficiently to be spreadable, or have a softening point, at a temperature no higher than 37, 35, 34, 33 or preferably 32° C. In preferred embodiments such compositions and unit dosage forms soften sufficiently to be spreadable or have a softening point in the range of 25-37, 25-35, 25-32, 27-32, 2832 and preferably 30-32° C. The solid compositions and unit dosage forms employed in accordance with the invention can have melting points that are below their softening points, for example by 1-4° C. (a composition's melting point is the temperature at which its viscosity begins to drop rapidly with each incremental increase in its temperature). In certain preferred embodiments, solid compositions and unit dosage forms employed in accordance with the invention become substantially liquid when heated to a physiological temperature, for example a temperature of 37° C., or even a temperature of as low as 35, 34 or 33° C. When substantially liquid, such compositions or dosage forms preferably have a viscosity of less than 100, or even less than 10 centipoise.

The softening points and melting points of solid compositions and unit dosage forms employed with applicators in accordance with the invention can be determined by DSC measurements. For example, a negative heat flow, or exotherm, from the calorimeter is often indicative of a material undergoing phase transition from solid to liquid as it's temperature is raised.

When placed in continuous contact with the desired skin region a solid composition or unit dosage form, preferably, will soften to a consistency to effect substantial application of the unit dose onto the desired skin region within a time period of less than 10, 5 or, preferably, 2 minutes. Solid compositions and unit dosage forms in accordance with the invention can have a softening point of not higher than the skin temperature of a living human or animal. Solid unit dosage forms in accordance with the invention can have an aspect ratio (wall: face) of less than 1:1.

The solid unit dosage form can be attached to the applicator by either mechanical, physical or chemical means. This can be achieved by the application of pressure, heat or an adhesive agent, depending upon the characteristics of the solid unit dosage form. Thus, the solid unit dosage form can be formulated so that it can be coupled to the receiving means by a process involving heating and melting or softening a surface of the dosage from, contacting that surface with the receiving means and cooling the resulting assembly to harden the melted or softened portion of the dosage form and cause it to become bonded to the receiving means. This characteristic is especially useful when the receiving means includes one or more raised portions, as it facilitates the penetration of such a portion or portions into the dosage form. Adhesives suitable for fixing solid unit dosage forms in place include polydimethylsiloxane, collodion, cyanoacrylates and polymers of acrylic acid, including polyacrylamides and polymethacrylates.

The spreadable composition, in any form, is preferably a pharmaceutical composition or formulation that, preferably, comprises a unit dose or a measured dose of a pharmaceutically active agent and, optionally, a pharmaceutically acceptable carrier. The pharmaceutically active agent is preferably therapeutically active. In preferred embodiments, the spreadable composition is a pharmaceutical composition or formulation as described in published international patent application no. WO 02/00203 A1.

When placed in continuous contact with the desired skin region, such pharmaceutical compositions or formulations, preferably, will soften to a consistency to effect substantial application of the unit dose of said pharmaceutically active agent onto a desired skin area of the living being within a time period of less than 10, 5 or, preferably, 2 minutes. In accordance with another aspect of this embodiment, the formulation or composition comprises a carrier medium for the pharmaceutically active agent, said carrier medium having a softening point of not higher than skin temperature of a living human or animal body.

Applicators in accordance with the present invention that include a unit or measured dose of spreadable composition, for example in the form of a solid unit dosage form such as a tablet, can be packed in sealed containers. Preferably, such applicators are each packed in an individual such sealed container. Such containers, preferably, are provided in an array comprising a plurality individually sealed containers, each including a single applicator and unit or measured dose of spreadable composition. An example of such an array is a conventional blister pack. When so packaged, an applicator and composition can be maintained in a sterile environment, preferably in isolation from atmospheric oxygen and pollutants. Packaging applicators in accordance with the invention in this manner increases their shelf life and prevents the spreadable composition from becoming prematurely oxidised or degraded. Blister packaging can be carried out in a nitrogen atmosphere to provide further resistance to degradation on storage.

In a further aspect, the present invention relates to a method of treating a human or animal body, comprising applying a spreadable composition to the skin or other external part of said body with an applicator in accordance with the invention.

In another aspect, the invention provides a kit comprising an applicator in accordance with the invention that is not coupled with a spreadable composition and at least one separately packaged unit dosage form. Kits in accordance with the invention can include instructions for coupling the composition to the applicator for use.

The term "living being", wherever used in this specification, should be understood to mean a living human or animal body. The preferred such being or body is a mammalian patient, preferably, a human patient.

In accordance with an embodiment of the present invention, a device for topically treating a desired skin region of a living being is provided. The device includes a unit dose of a pharmaceutical formulation and an applicator having a first portion coupled to the unit dose and a second portion configured for being held by a user. The formulation includes a therapeutically effective amount of a therapeutic agent and a pharmaceutically acceptable carrier medium therefor. In accordance with one aspect of this embodiment, the formulation is solid at ambient temperature and has a softening point of not higher than 35, 34, 33, or 32° C., such that when the formulation is placed in continuous contact with the desired skin region, it is softened to a consistency to effect substantial application of the unit dose onto the desired skin region within a time period of less than 10, 5 or 2 minutes. In accordance with another aspect of this embodiment, said formulation has a softening point of not higher than skin temperature of the living being, said formulation having an aspect ratio (wall:face) of less than 1:1. In accordance with yet another aspect of this embodiment, said formulation, upon being placed in continuous contact with the skin of the living being, is softened to a consistency to effect substantial application of said therapeutically effective amount of said therapeutic agent onto a desired skin area of the living being within a time period of less than 10, 5 or 2 minutes. In accordance with still another aspect of this embodiment, the formulation comprises a carrier medium having a softening point of not higher than skin temperature of the living being. Preferably, the living being is a mammalian patient, and most preferably, the mammalian patient is human.

The user may apply the unit dose to the user's own skin, or to that of another living being.

The device may also include an intermediate member attached to the unit dose, and the first portion of the applicator may be configured to be removably attachable to the intermediate member.

In accordance with another embodiment of the present invention, a method for topically treating a desired skin region of a living being is provided. The method includes coupling a unit dose of a pharmaceutical formulation to a first portion of an applicator, holding a second portion of the applicator, spreading the unit dose of the pharmaceutical formulation on the desired skin region without contacting the unit dose with a skin region outside the desired skin region. The formulation includes a therapeutically effective amount of a therapeutic agent and a pharmaceutically acceptable carrier medium therefor. In accordance with one aspect of this embodiment, the formulation is solid at ambient temperature and has a softening point of not higher than 35, 34, 33 or 32° C., such that when the formulation is placed in continuous contact with the desired skin region, it is softened to a consistency to effect substantial application of the unit dose onto the desired skin region within a time period of less than 10, 5 or 2 minutes. In accordance with another aspect of this embodiment, said formulation has a softening point of not higher than skin temperature of the living being, said formulation having an aspect ratio (wall: face) of less than 1:1. In accordance with yet another aspect of this embodiment, said formulation, upon being placed in continuous contact with the skin of the living being, is softened to a consistency to effect substantial application of said therapeutically effective amount of said therapeutic agent onto a desired skin area of the living being within a time period of less than 10, 5 or 2 minutes. In accordance with still another aspect of this embodiment, the formulation comprises a pharmaceutically acceptable carrier medium having a softening point of not higher than skin temperature of the living being. Preferably, the living being is a mammalian patient, and most preferably, the mammalian patient is human.

In accordance with a yet further embodiment of the present invention, a device for topically treating a desired skin region of a living being is provided. The device includes an applicator member including a surface having indicia of measurement thereon, with a grip extending from the applicator member. The surface is configured to receive a measured dosage of a pharmaceutical formulation in extruded form. In such devices, the grip is preferably configured to be held by a user and to enable the user to move the applicator member with respect to the desired skin region so as to apply and spread the measured dosage over the desired skin region.

The device can include the dosage of the pharmaceutical formulation, extruded and measured as described above. The desired skin region is preferably larger than the surface of the applicator member, which can be substantially planar, or can be at least partially convex.

The pharmaceutical formulation can include a therapeutically effective amount of a therapeutic agent and a pharmaceutically acceptable carrier medium therefor. It can be in the form of an ointment or a gel, or some other form that enables extrusion such as from a tube or dispenser.

The applicator member and the grip can be of integral construction. The applicator can include a non-absorptive material. At least one of the applicator member and the grip can include a moulded plastic material.

The surface of the applicator member can be configured to receive the pharmaceutical formulation from a tube. The applicator member and the grip are preferably configured to enable the application and the spreading without contacting the pharmaceutical formulation with a skin region outside the desired skin region.

The user can be the living being, or can be a second living being. The indicia of measurement can include spaced markings, and the spaced markings can, for example, include raised ridges, indented ridges, or printed lines.

In accordance with a still further embodiment of the present invention, a method for applying a pharmaceutical formulation to a desired skin region of a living being is provided. The method includes extruding an amount of the pharmaceutical formulation onto a surface of an applicator member of a spreading device. The surface of the applicator member includes indicia of measurement. The extruding is performed so as to obtain a measured dosage of the pharmaceutical formulation using the indicia of measurement. The method also includes the step of gripping a grip of the spreading device, wherein the grip extends from the applicator member, and moving the grip with respect to the desired skin region so as to apply and spread the measured dosage over the desired skin region.

The measured dosage can, for example, be extruded from a tube of the pharmaceutical formulation. The gripping and the applying can be performed by a user without contacting the measured dosage with a skin region outside the desired skin region. The desired skin region is preferably larger than the surface of the applicator member, which can be substantially planar, or can be at least partially convex.

The indicia of measurement can include spaced markings, which can include, for example, raised ridges, indented ridges, or printed lines. The extruding step is preferably performed attendant to the moving step.

Where alternative values for parameters such as temperature and time are given in this specification, each such alternative should be understood as being an individually preferred value, or embodiment of the invention.

DESCRIPTION OF DRAWINGS

FIGS. 2a, 2b, 2c and 2d show a device according to a second embodiment of the present invention.

FIGS. 3a, 3b and 3c show a device according to a third embodiment of the present invention.

FIGS. 6a, 6b, 6c and 6d show a device according to a sixth embodiment of the present invention.

FIGS. 7a, 7b and 7c show a device according to a seventh embodiment of the present invention.

FIGS. 8a, 8b and 8c show a device according to an eighth embodiment of the present invention.

DESCRIPTION OF PREFERRED EMBODIMENTS

Figure 1A:
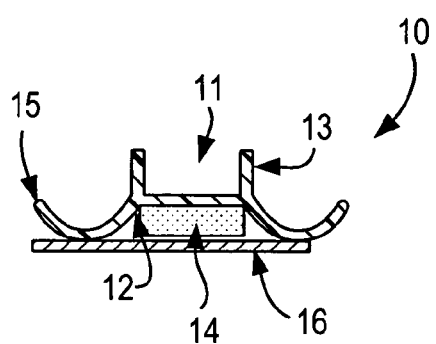
FIGS. 1a, 1b, 1c and 1d show a device for topically treating the skin of a human or animal body according to one embodiment of the present invention.

With reference to FIG. 1a, a device 10 for topically treating the skin of a human or animal body according to a first embodiment of the present invention is shown. An applicator 11 has first portion 12 and second portion 13. First portion 12 is coupled to unit dose 14 of a pharmaceutical formulation. Second portion 13 is configured to be held by a user so as to enable the user to spread the unit dose onto the desired skin region without the unit dose contacting a skin region outside of the desired skin region (for example, the skin of the user's hand). Flexible flange 15 of applicator 11 is disposed between first portion 12 and second portion 13 and aids in preventing contact between the unit dose and the user. The flexibility of the flange 15 enables the application to be pushed down onto the skin in a closed environment. The devices may be manufactured and processed so as to be attached to one another for more convenient packaging.

Figure 1B:
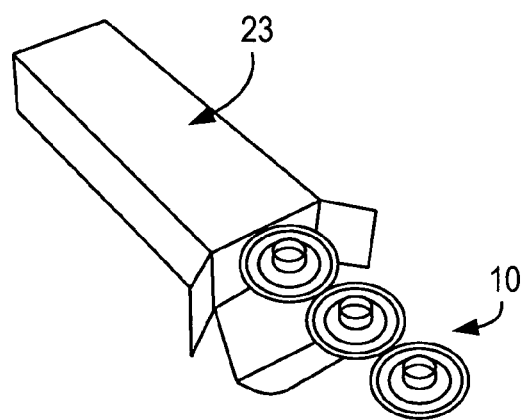
Figure 1C:
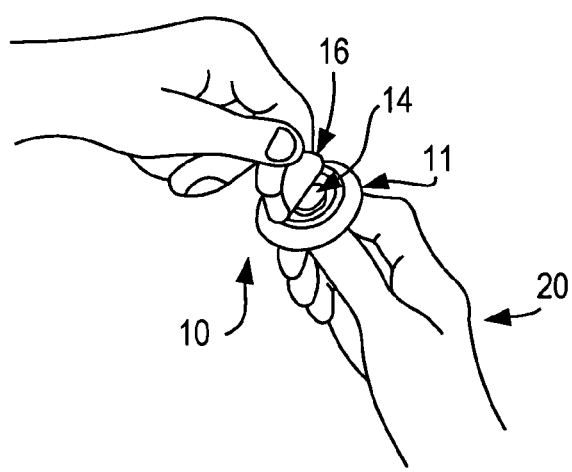
Figure 1D:
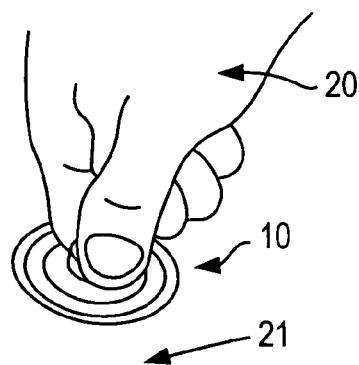

As shown in FIG. 1b, several devices 10 may be attached to one another and packaged in a box 23. The user may detach a single device from a strip of devices. The user 20 may then peel back a layer of protective material (for example, a foil) 16 from the device 10 as shown in FIG. 1c. The protective layer acts to seal the unit dose of the pharmaceutical formulation from the outside atmosphere, for example, to prevent any of the pharmaceutical formulation from prematurely escaping from the applicator, to prevent undesired chemical interactions with the environment, and to prevent impurities from entering into the unit dose. As can bee seen in FIG. 1d, the user 20 may grip the second portion 13 of the applicator 11 in order to conveniently spread the unit dose onto the desired skin region 21.

Figure 2A:
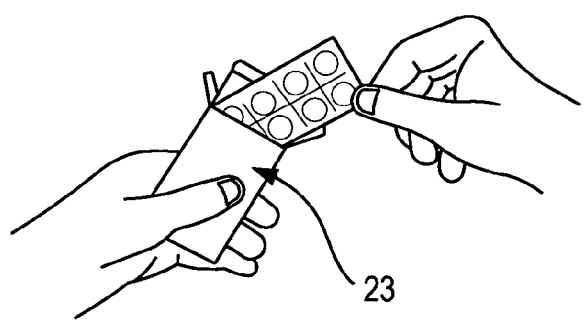
Figure 2A:
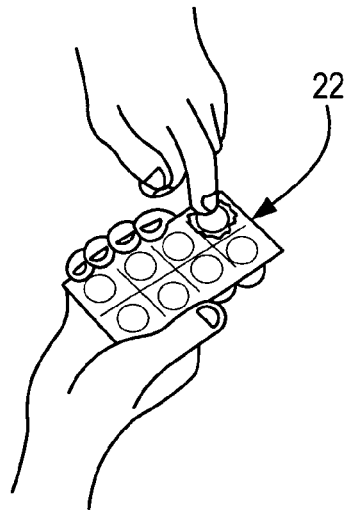
Figure 2B:
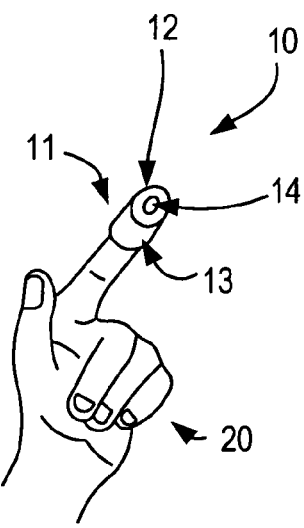
Figure 2B:
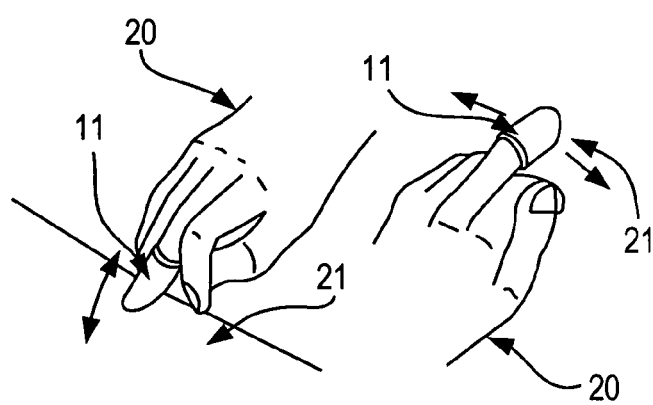

FIGS. 2a and 2b show a device according to a second embodiment of the present invention packaged inside blister pack 22 and box 23. Blister packs are commonly used to package pharmaceutical products. They provide protection from the outside environment and preferably also keep the products sterile. An additional protective layer 16 (for example, a foil) may be provided on the applicator 11 to provide additional protection of the unit dose from the outside environment as shown in FIG. 1. As is shown in FIGS. 2c and 2d, the applicator 11 according to the second embodiment has first portion 12 coupled to unit dose 14 and second portion 13 that is generally cylindrical in shape. Second portion 13 is configured to fit around a finger of the user to aid in holding the applicator and spreading the unit dose on the desired skin region 21.

Figure 3C:
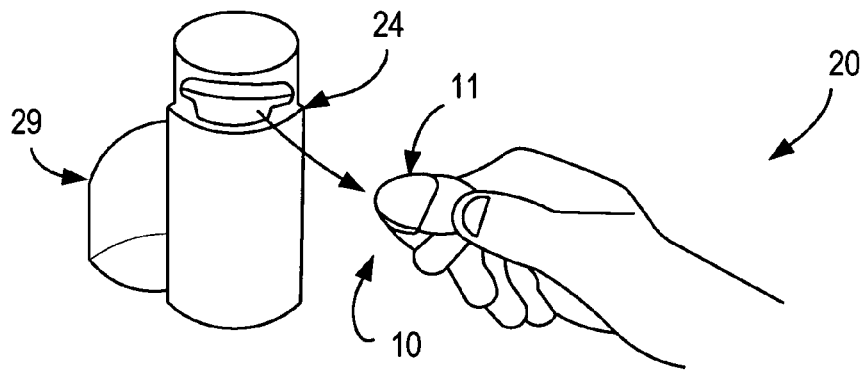
Figure 3C:
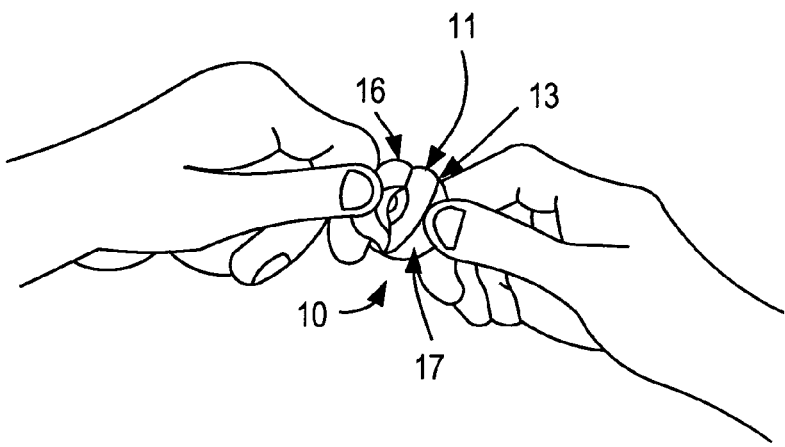
Figure 3C:
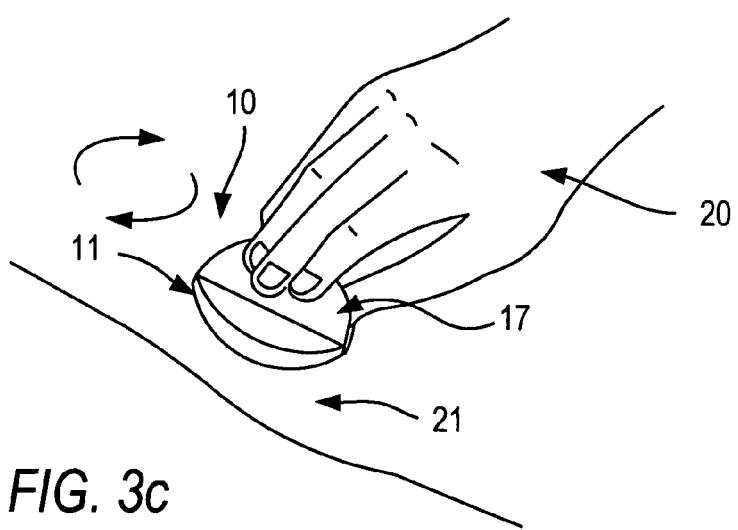

As is shown in FIG. 3a, the device according to a third embodiment of the present invention is substantially disk-shaped, though the device and the unit dose can have any shape. The flat shape of the device 10 enables the devices to be stacked vertically and packaged in a dispenser top 29. In this illustration, the dispenser 24 is cylindrically shaped and the devices 10 are disc shaped. After removing a device from the dispenser, the user 20 may peel off the protective layer 16 (for example, a foil) from the device 10 as shown in FIG. 3b. Second portion 13 of applicator 11 includes a fold-up tab 17 to enable the user to grip the applicator and aid in spreading the unit dose 14 as shown in FIGS. 3b and 3c. The unit dose is preferably spread by moving in a generally circular motion on the desired skin region.

Figure 4A:
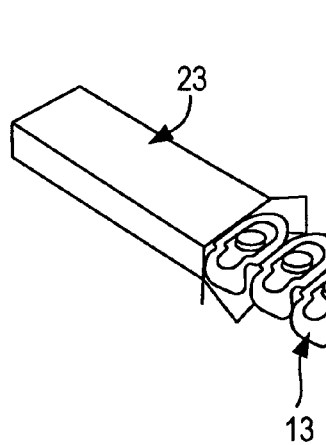
FIGS. 4a, 4b and 4c show a device according to a fourth embodiment of the present invention.
Figure 4B:
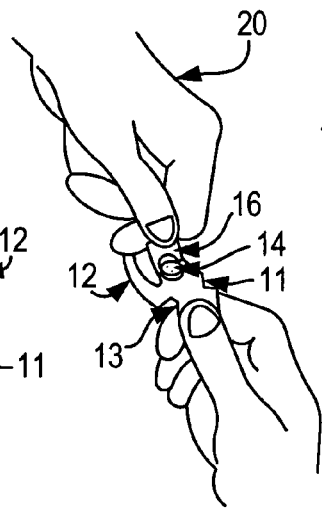
Figure 4C:
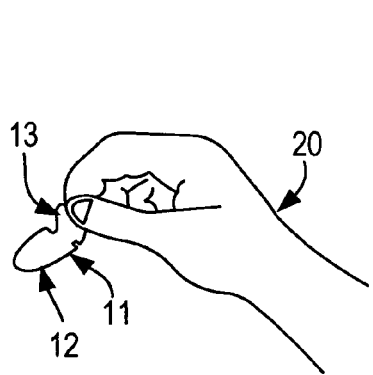

FIGS. 4a, 4b and 4c show a fourth embodiment of the present invention. In this embodiment, the first portion 12 and the second portion 13 are in the same plane and formed by a single strip of material. The second portion 12 is a tab extending from the first portion and can be bent upward to enable the user to better spread the unit dose. The applicator 11 according to this embodiment has a narrow form that is suitable for treating small, or hard to reach skin regions.

Figure 5A:
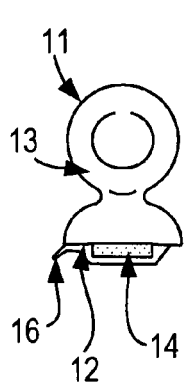
FIGS. 5a, 5b and 5c show a device according to a fifth embodiment of the present invention.
Figure 5B:
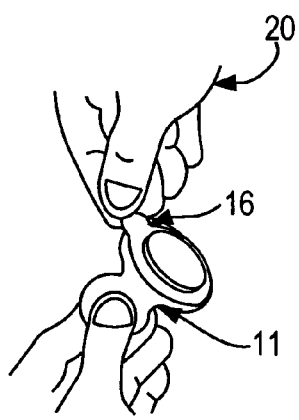
Figure 5C:
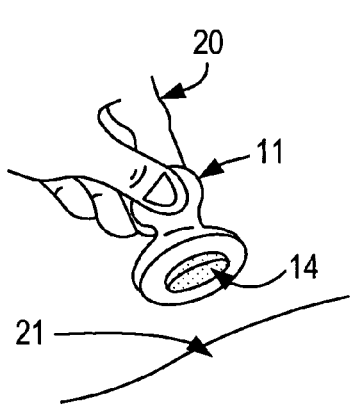
Figure 9A:
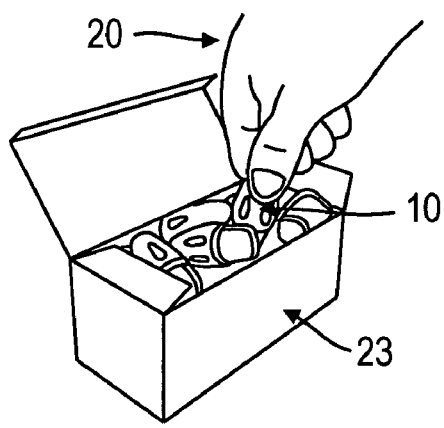
FIGS. 9a, 9b, 9c and 9d show a device according to ninth embodiment of the present invention.
Figure 9B:
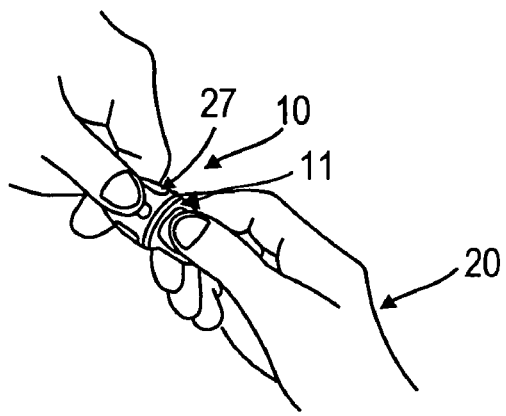
Figure 9C:
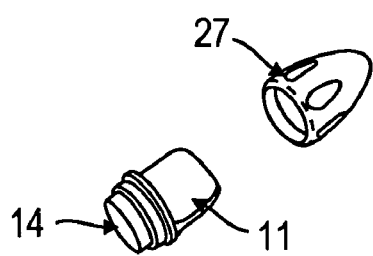
Figure 9D:
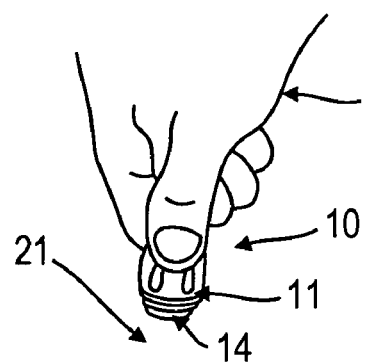
Figure 10A:
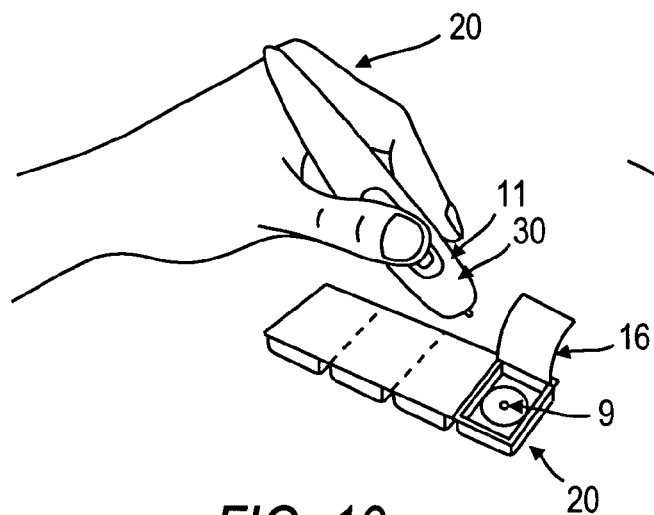
FIGS. 10a, 10b, 10c and 10d show a device according to a tenth embodiment of the present invention.
Figure 10B:
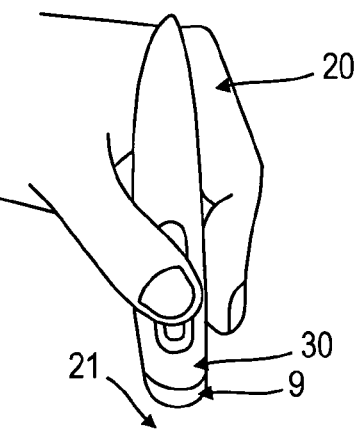
Figure 10C:
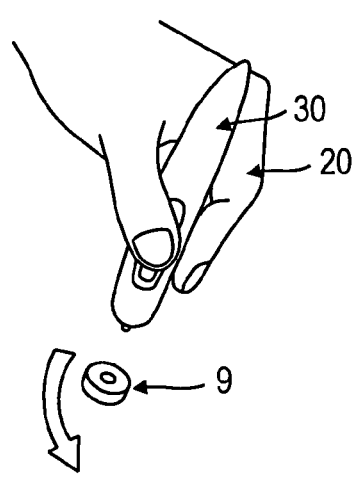
Figure 10D:
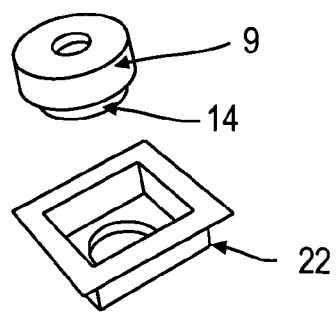

As shown in FIGS. 5a, 5b and 5c, the device according to the fifth embodiment includes an applicator 11 having a second portion 13 that extends perpendicular from the desires skin surface 21 as the unit dose is being applied. In addition, this device includes a larger gripping area than the device of FIGS. 4a, 4b and 4c. As illustrated, the gripping area is rounded and flat. However, other arrangements can alternatively be used. In any event, after peeling off the protective layer 16 (for example, a foil), the user may spread the unit dose 14 into the desired skin region 21.

FIGS. 6a, 6b, 6c and 6d show a sixth embodiment of the present invention in which the device is packaged in a continuous strip of devices 26. Dispenser 24 is configured to dispense a single device at a time. The unit doses can be advanced in the dispenser manually, by pulling the last dose in the continuous roll 26 forward, or the dispenser can include an advancing device such as a rotatable drum actuated by a dial, or other actuation member. After tearing a device 26 from dispenser 24, the user may tear open protective wrapper 25, remove the device and spread the unit dose onto the desired skin region 21 by holding application 11.

FIGS. 7a, 7b and 7c show a seventh embodiment of the present invention, in which the applicator 11 includes a rigid elongated tab. This shape aids in holding the applicator 11 for removing the layer 16 and for the spreading of the unit dose 14 onto the desired skin region 21.

The devices according to an eighth embodiment of the present invention, as shown in FIGS. 8a, 8b, and 8c are individually wrapped and packaged in box 8a. The user removed the protective wrapper 25. The applicator 11 in this embodiment is generally cylindrical in shape.

A device according to a ninth embodiment of the present invention is shown in FIGS. 9a, 9b, 9c and 9d and uses a protective shield 27 instead of a protective layer 16 to seal the unit dose from the outside environment. The user 20 can remove the protective shield 27, such as, for example, by twisting or pulling it off (e.g., threaded or friction fit). The protective shield 27, which is made of a stiff plastic, is configured to fit onto the applicator 11 to aid the user in holding applicator 11 for spreading unit dose 14 onto the desired skin region 21.

According to a tenth embodiment of the present invention, as shown in FIGS. 10a, 10b, 10c and 10d, the applicator includes an applicator instrument 30. The applicator instrument 30 may be pen-shaped. It is configured to be removably attached either directly to a unit dose 14, or to an intermediate member 9 that is directly attached to the unit dose 14. In this latter case, a protrusion (for example, a pin) is inserted into a fitting hole in intermediate member 9. The user should hold the intermediate member 9 using the applicator instrument 30 for spreading unit dose 14 onto the desired skin region 21. After the unit dose 14 has been applied to the desired skin region, the user may dispose of intermediate member 9 (and any unused portion of unit dose 14) from the applicator instrument 30, such as by activating a lever on applicator instrument 30.

Figure 11A:
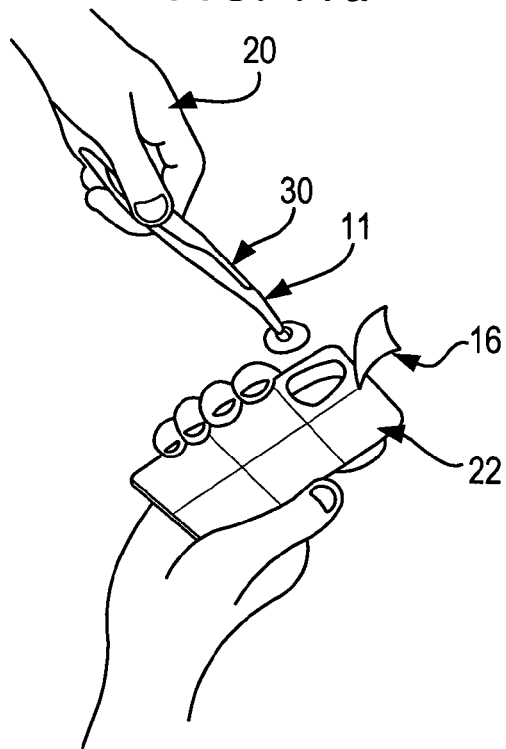
FIGS. 11a, 11b and 12 show a device according to an eleventh embodiment of the present invention.
Figure 11B:
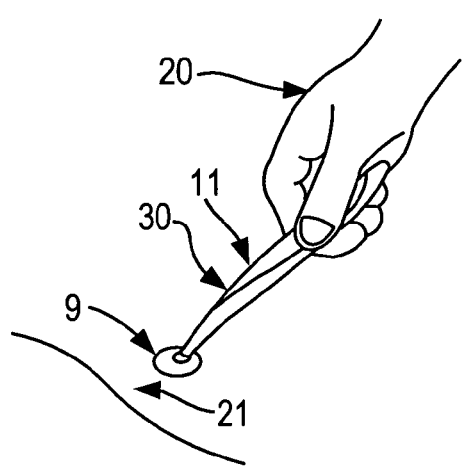
Figure 12:
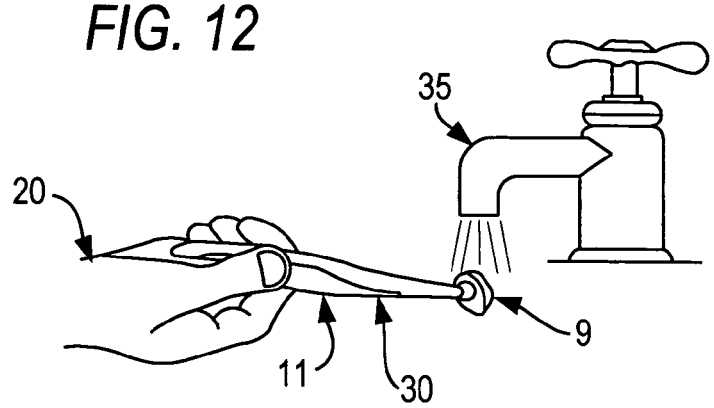

According to an eleventh embodiment of the present invention, as shown in FIGS. 11a, 11b and 12, the applicator 11 may include another type of applicator instrument 30. In this embodiment, the applicator instrument 30 and intermediate member 9 are connected to form a one-piece instrument. The user peels back a protective layer 16 from a blister pack 22. The applicator instrument 30 is held by the user and the intermediate member 9 is pressed onto a unit dose within the blister pack 22. The intermediate member 9 adheres to the unit dose and the user spreads the unit dose onto the desire skin region as shown in FIG. 11b. After the unit dose has been substantially applied to the desired skin region, the user washes any excess pharmaceutical formulation from the intermediate member 9 and applicator instrument 30, for example by holding it under a running faucet 35.

Figure 13:
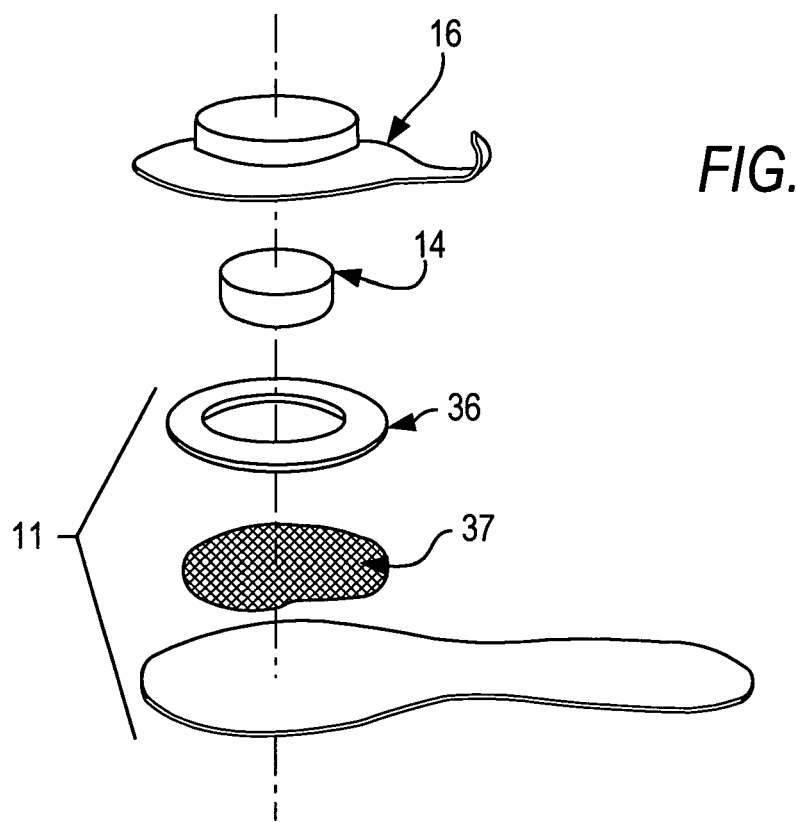
FIG. 13 shows one configuration for coupling a unit dose to an applicator according to the present invention.
Figure 14:
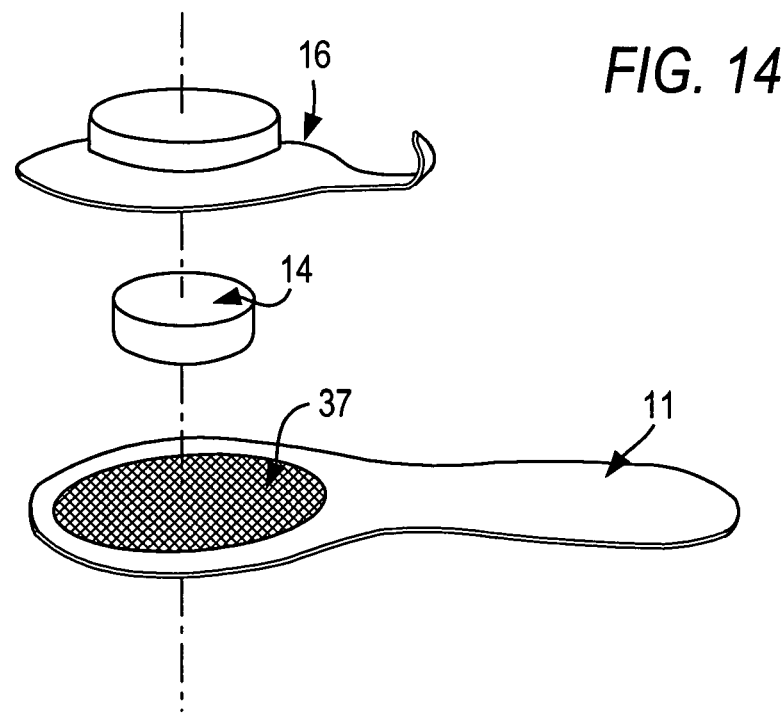
FIG. 14 shows a second configuration for coupling a unit dose to an applicator according to the present invention.

FIGS. 13 and 14 show two example of how a unit dose 14 and protective layer 16 may be coupled to an applicator 11. In the example of FIG. 13, the applicator 11 includes fine mesh material 37 and adhesive ring 36 and the protective layer 16 is made of foil. The adhesive ring 36 enables the foil layer 16 to adhere to the applicator 11 and to seal the unit dose 14 from the outside environment. The fine mesh material 37 provides a high level of friction between itself and the unit dose 14. Provided that the friction is greater than the friction between the unit dose and the skin, the unit dose should not slip away. In the example shown in FIG. 14, the applicator 11 includes a portion of fine mesh that is moulded into the applicator itself.

Figure 15A:
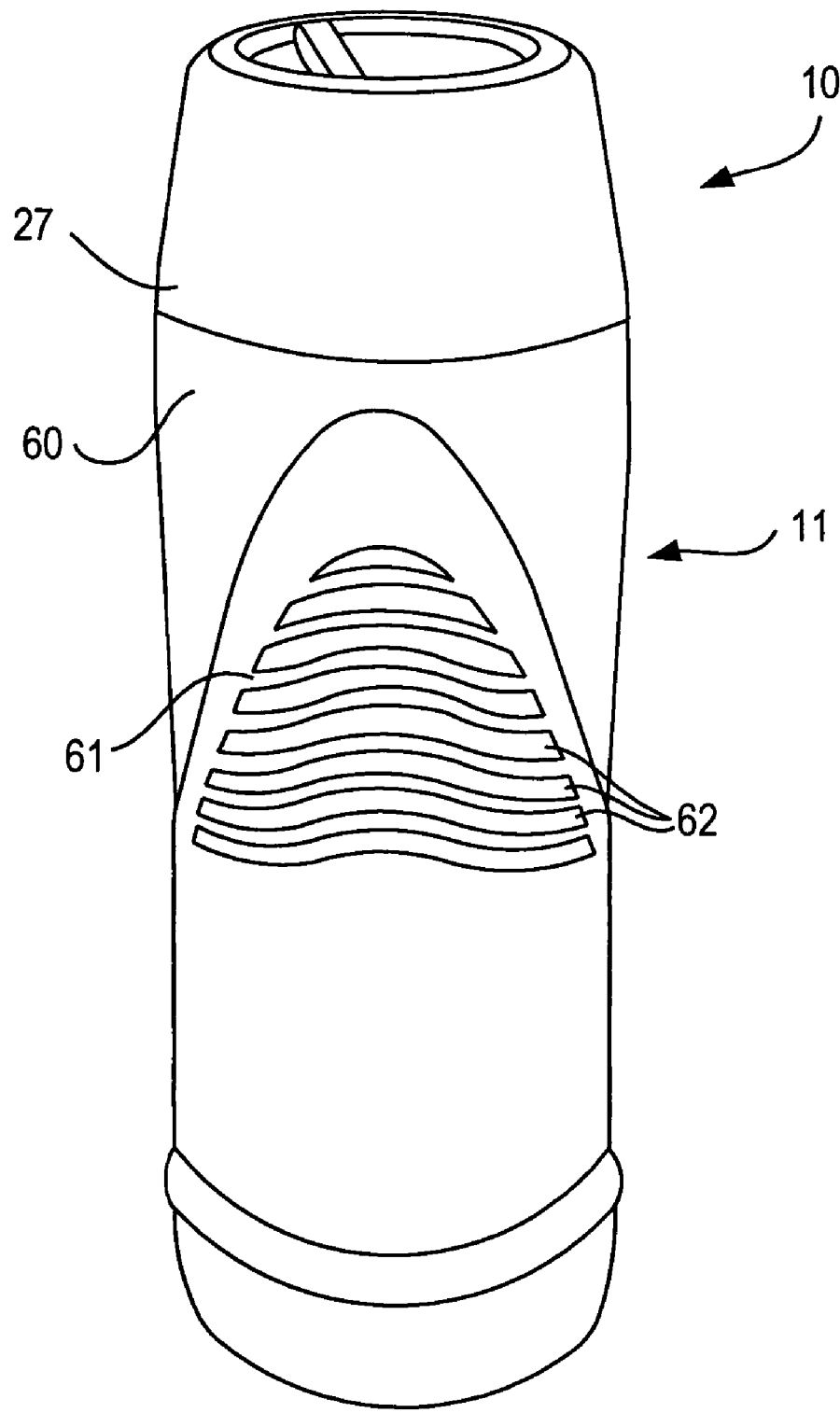
FIGS. 15a, 15b, 15c, 15d and 15e show a device according to a twelfth embodiment of the present invention.
Figures 15B, 15C, 15D:
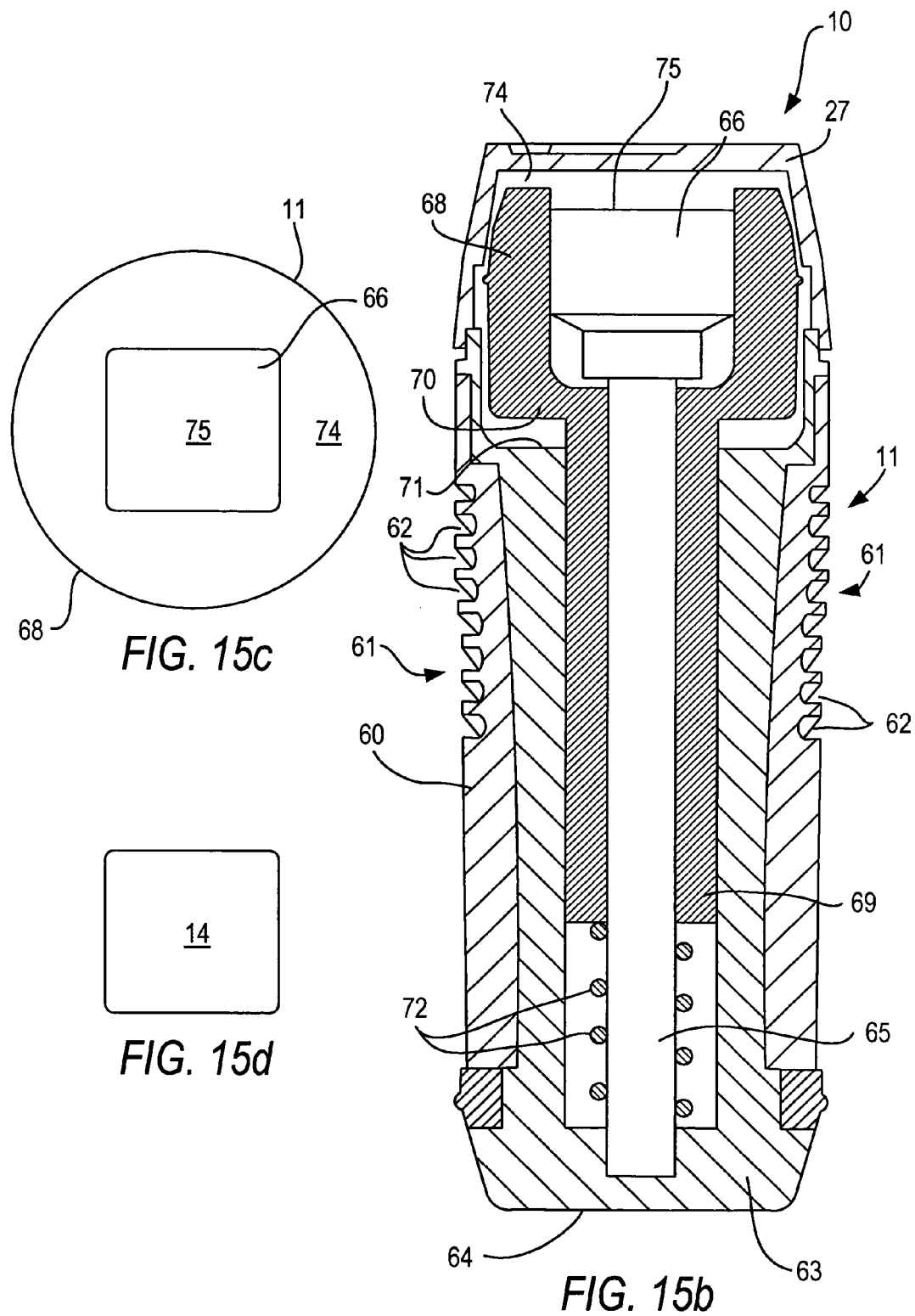
Figure 15E:
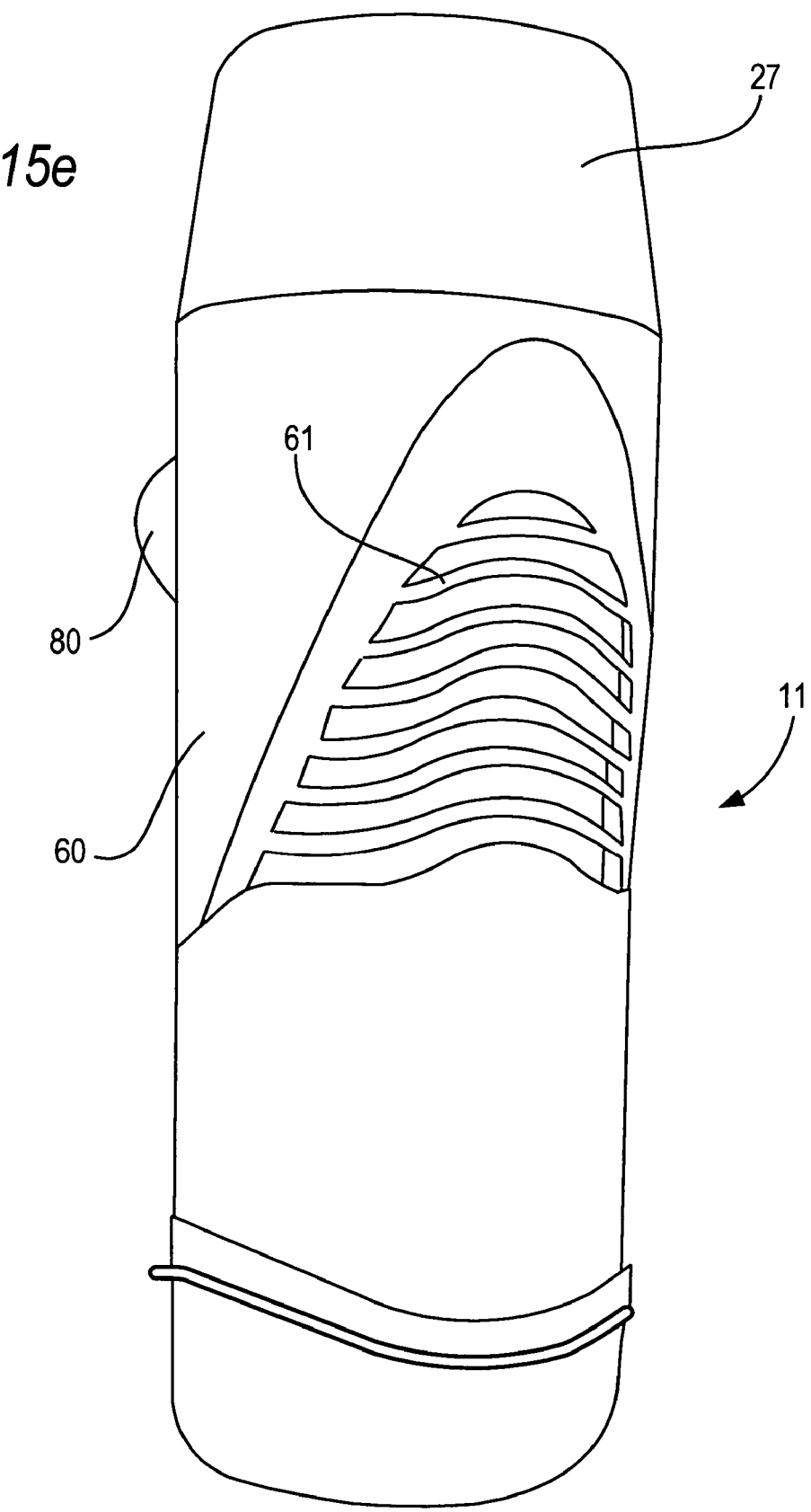

FIG. 15a shows a side view of a device 10 according to a twelfth embodiment of the present invention and FIG. 15b shows a section through the device shown in FIG. 15a. Referring to FIGS. 15a and 15b, the device 10 includes an applicator 11 that can be of any suitable size, but is preferably around 6-7 cm in length with a diameter of about 2-2.5 cm so that it can be conveniently held in the human hand. The applicator 11 includes a substantially cylindrical body 60 provided with opposed outwardly facing gripping surfaces 61, each comprised of an array of substantially parallel grooves 62, located mid way along its length. The body 60 is hollow and closed at a first axial extremity by a base portion 63, which defines an outwardly facing foot 64, upon which the device 10 can be stood (as shown in FIG. 15a). A cylindrical rod 65 extends from the base portion 63 coaxially within the body and supports a tablet mounting block 66, which protrudes in an axial direction beyond an open second axial extremity 67 of the cylindrical body 60. An outwardly substantially cylindrical platform 68 is integrally formed with a sleeve member 69 and the latter is located in sliding engagement about the rod 65. The platform 68 surrounds the mounting block 66 and partially protrudes from the open second axial extremity 67 of the cylindrical body 60. Where the platform 68 joins the sleeve member 69 it defines a radially inwardly extending flange 70. A radially inwardly extending step 71 is defined within the body 60. The flange 70 and step 71 are dimensioned and arranged so as to restrict the sliding movement of the platform 68 and sleeve 69 to between an extended position, in which the flange 70 contacts a step 73 (defined at the junction of the tablet mounting block 66 and the rod 65) and the outer face 75 of the block 66 is recessed within the platform 68 (as is shown in FIG. 15b), and a retracted position, in which the flange 70 contacts the step 71 and the axially outermost faces 74 and 75 of the platform 68 and mounting block 66 are substantially flush. A helical compression spring 72 surrounds the rod 65 and acts between the sleeve 69 and the base potion 63 of the body 60 and biases the assembly of the sleeve 69 and platform 68 into the extended position, with the tablet mounting block 66 recessed within the platform 68, as shown in FIG. 15b. A removable cover 27 is removably secured to the body 60 via, for example, a friction fit or screw threaded engagement. In an alternative arrangement, shown in FIG. 15e, the cover 27 is held in place by a latching mechanism (not shown in detail) that releasably engages the cover to the body 60 and which is actuated by a button 80. The button 80 protrudes from the body 60, adjacent to the cover 27, and pressing the button 80 releases the cover 27.

FIG. 15c shows the top (as orientated in FIG. 15b) face of the applicator 11 with the cover 27 removed and FIG. 15d shows a top view of a rectangular cuboidal tablet shaped unit dose form 14 suitable for use in the applicator 11 shown in FIGS. 15a and b. As can be seen in FIGS. 15c and 15d, the unit dose form is dimensioned so as to fit onto the outer face 75 of the tablet mounting block 66 with the platform 68 in the extended position shown in FIG. 15b. Although this cannot be seen in the figures, the unit dose form 14 is sufficiently thick so as to protrude outwardly from the outer face 74 of the platform 68 a short distance when it is so located. However, less than half of the thickness of the unit dose form will so protrude and the remainder will be located within the confines of the platform 68.

The device 10 should be stored with the cover 27 in place protecting the platform 68 and tablet mounting block 66. To use the device, a user should firstly remove the cover 27 and then place a tablet 14 onto the outer face 75 of the tablet mounting block 66. Holding the body 60 of the device by the gripping surfaces 61, he should then bring the device 10 into contact with the skin such that the exposed face of the tablet 14 is pressed into contact with the skin. In most cases, the tablet 14 will be composed of a formulation that is solid at ambient temperatures (of around 20-25° C.), but which will melt and soften at or below physiological temperatures (of around 37° C.; the tablet having a softening point of between 30 and 35° C.). Thus, on being pressed into contact with the skin, the tablet 14 will begin to melt and soften and can be spread onto the desired area of the skin by the user rubbing the tablet across it. The tablet 14 is prevented from being bodily displaced from the tablet mounting block 66 by the surrounding platform 68. When the tablet 14 has been eroded until its exposed face is flush with the outer face 74 of the platform 68, the user continues to press the tablet 14, and now the surrounding outer face 74 of the platform 68, into contact with the skin and rub them across the skin. This causes the tablet 14 to further erode and the platform 68 to be pushed back into the body 60 against the force exerted by the spring 72. However, the force exerted by the spring 72 is sufficient to ensure that the platform 68 always protrudes sufficiently from the mounting block 66 to support whatever remains of the tablet 14 and to prevent it from being bodily displaced from the mounting block 66. Since the platform can be pushed into the body 60 until its outer face 74 is flush with the outer face 75 of the tablet mounting block 66, all of the tablet 14 can be spread onto the skin in this controlled manner.

In an alternative embodiment, the applicator can include a dispenser within the body 60 for holding a plurality of unit doses and dispensing them, one at a time, into the position for applying the unit dose.

Figure 16:
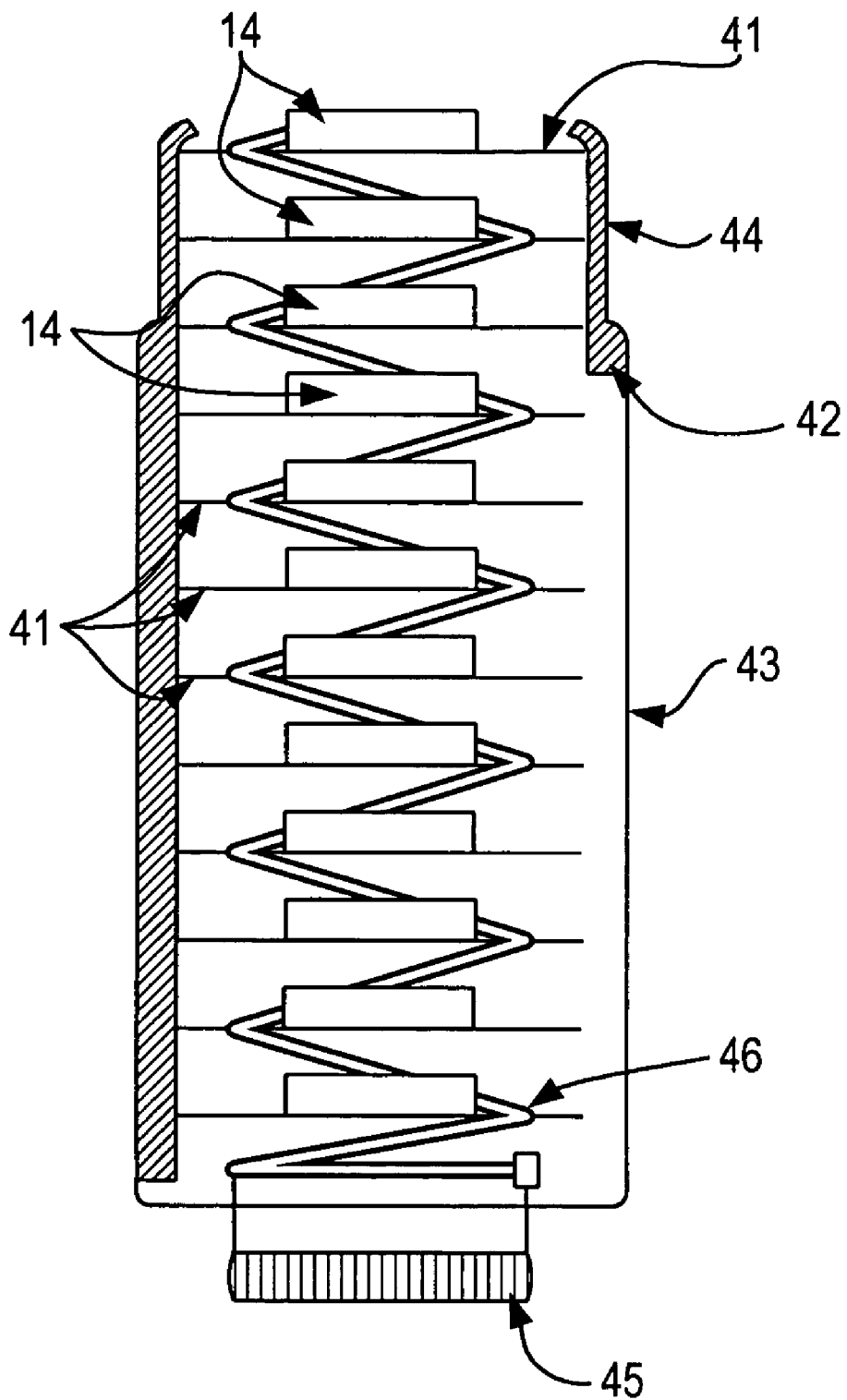
FIG. 16 shows a mechanical advance system for use with an applicator according to a thirteenth embodiment of the present invention.
Figure 17:
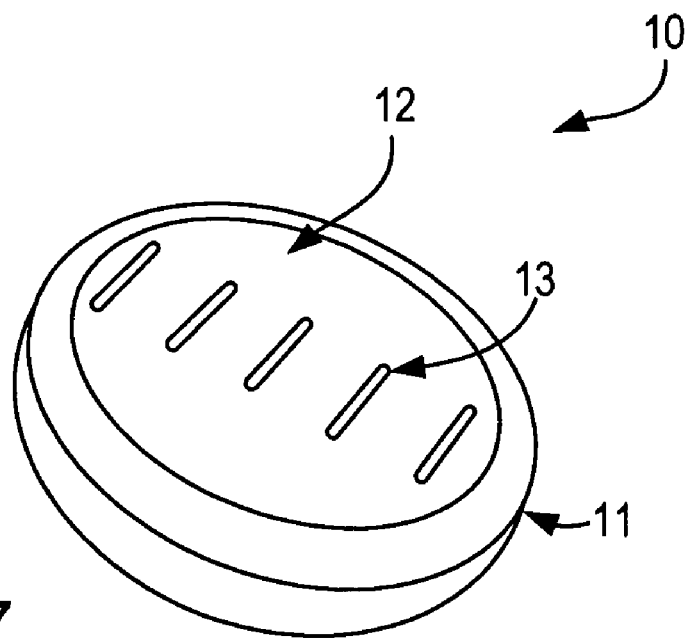
FIG. 17 shows a perspective view of a bottom portion of an application device according to a fourteenth embodiment of the present invention.
Figure 18:
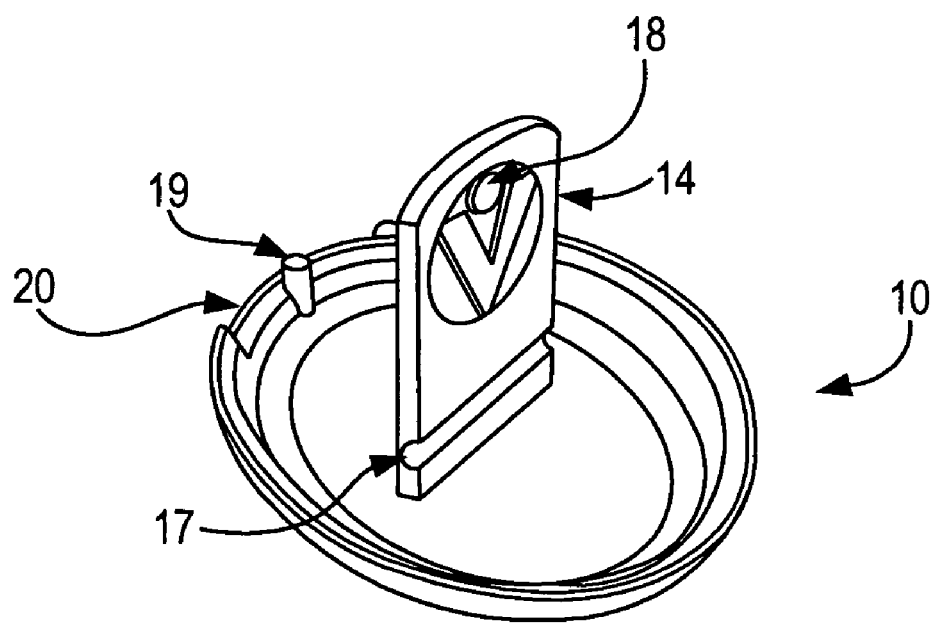
FIG. 18 shows a perspective view of a top portion of the applicator device shown in FIG. 17.
Figure 19:
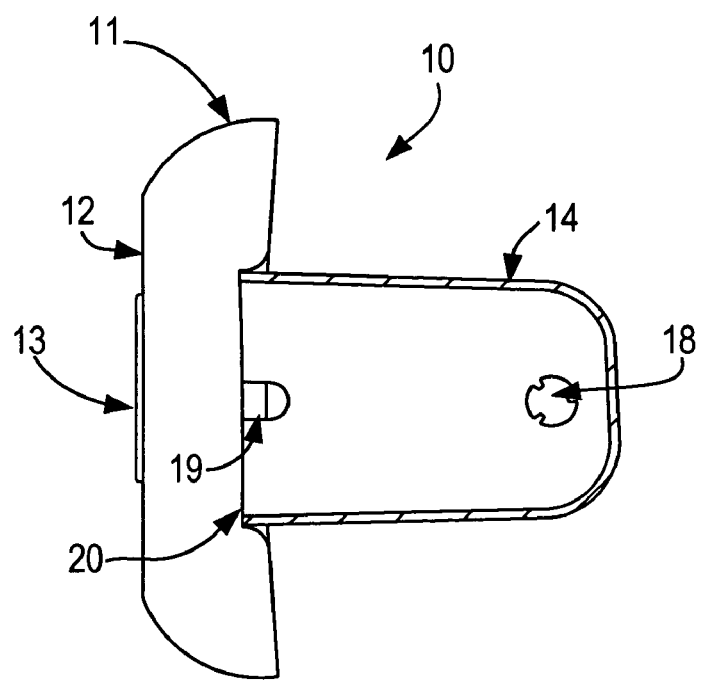
FIG. 19 shows a side view of the applicator device shown in FIG. 17.

Such a dispenser may be actuated, for example, by rotating a dial at the base of the dispenser and an example of such a multidose applicator is shown in FIG. 16. A plurality of unit doses 14 are each attached to a substrate 41 and disposed in a stacked formation. Dispensing mechanism 43 includes an annular housing 47, which surrounds the stack of unit doses 14, and substrates 41. A spiral member 46 is disposed lengthwise inside the annular housing. The size and shape of the spiral member are such that the unit doses fit within the diameter of the spiral member, but the substrates do not. The user may rotate the spiral member 46, for example, by manually rotating dial 45. Each revolution of the spiral member advances the substrates carrying the unit doses one position in the upward direction. A pivotable clip 44 prevents the substrate from advancing past the end of the dispensing mechanism 43, and holds it in position for the user to apply the unit dose 14 on the desires skin region. When the unit dose 14 has been substantially applied by the user, the user may dispose of substrate 41, for example by opening pivotable clip 44 about pin 42. After substrate 41 has been removed, clip 44 can be pivoted back to its closed position, and spiral 46 can be rotated to advance the next substrate 41 and unit dose 14 into position for application. The embodiment of FIG. 16 is meant to illustrate one possible dispensing mechanism. It is understood that many similar mechanisms may be employed to dispense unit doses within an applicator.

Figure 20:
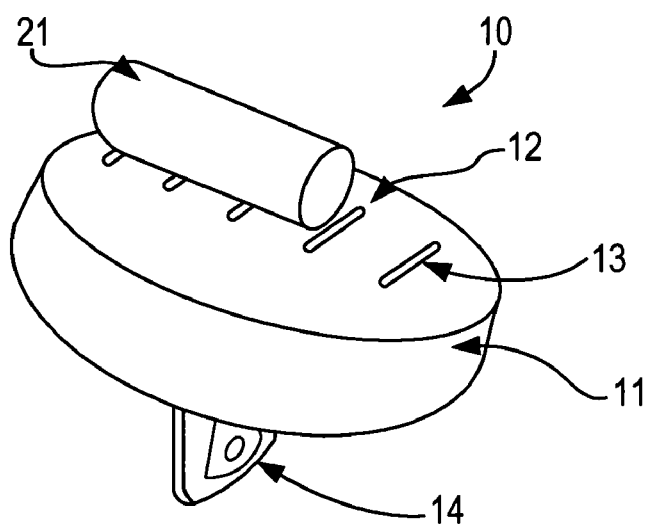
FIG. 20 shows a perspective view of the bottom portion of the device shown in FIG. 17, with a measured dosage of a pharmaceutical formulation applied to a surface.

A thirteenth embodiment of an application device 10 according to the present invention is depicted in FIGS. 17-20. The device 10 includes an applicator element 11 and a gripping element 14. The applicator element includes a surface 12, which in this embodiment is substantially planar. The surface 12 includes indicia of measurement in the form of raised ridges 13, which are spaced apart from one another in regular intervals. The indicia may also take another form, for example, of indented ridges or printed lines, and may be labelled, for example with numbers indicating a distance or other measurement amount. The embodiment shown in the drawings includes five ridges spaced at intervals of 0.5 fingertip units (FTU), which corresponds to 250 mg of pharmaceutical formulation (assuming a 5 mm nozzle or tube opening through which the formulation is extruded). FIG. 20 shows the device 10 including a measured dosage 21 of a pharmaceutical formulation. The measured dosage extends from the first edge to the fourth, thus spanning three measuring intervals (1.5 FTU's) and corresponds to 750 mg of the pharmaceutical formulation. The device 10 may also include more or fewer indicia of measurement with different interval amounts to facilitate different dosage needs, e.g., 0.10 FTUs, 0.20 FTUs, 0.25 FTUs, 0.3 FTUs, 0.4 FTUs etc. Moreover, other metrics can be substituted for FTUs, such as millimetres, centimetres, inches, etc.

The device shown in FIGS. 17-20 may be used as follows: A user extrudes an amount of a pharmaceutical formulation from a tube or other dispenser onto surface 12 of applicator member 11, while holding the device 10 using gripping member 14. Using the raised ridges, the user extrudes a measured dosage of the pharmaceutical formulation, by applying a bead of the pharmaceutical formulation starting at the first ridge and spanning the number of intervals that corresponds to the desired measured dosage. Once the measured dosage has been extruded onto the surface 10 of applicator member 11, the user then, by holding gripping member 14 and moving gripping member so that the applicator moves with respect to a desired skin region, applies the measured dosage 21 to the desired skin region, and spreads the measured dosage over the desired skin region until substantially all of the measured dosage is absorbed into the skin. The measured dosage is preferably spread by moving the device in a generally circular motion on the desired skin region. The relationship of the gripping member and the applicator member facilitates the applying and spreading of the measured dosage without any undesired contact between the pharmaceutical formulation and a skin region outside the desired skin region (for example, the user's fingers and hands).

The desired skin region may be a portion of the user's own skin, or may be that of another person (for example, when the user is a nurse or other health care professional applying a pharmaceutical formulation to a patient).

Preferably the device 10 is manufactured as a single piece device of integral construction, such as by injection moulding, so that the device 10 can be mass-produced with a very low unit cost of production. In the embodiment shown in FIGS. 17-20, gripping member 14 extends from the applicator element 11 from a side opposite the surface 12, and includes an indented portion 17, which enables the gripping member to fold to a closed position in which it is substantially parallel to surface 12. In the folded position, gripping member 14 fits into recess 20 of applicator member 11. Pin 19 of applicator member 11 fits into hole 18 of gripping member 14, in order to aid in holding gripping member in the closed position. The folding of the gripping member 14, greatly reduces the overall dimensions of the device (in the vertical direction), and facilitates packaging of the device. The device is preferably individually packaged to ensure that it is sterile at the time of user. The relatively flat overall shape of the device 10 enables many devices to be stacked relative to one another for convenient multiple packaging and for fitting into a dispenser, that could be conveniently used, for example, in a hospital or clinical setting.

Figure 21:
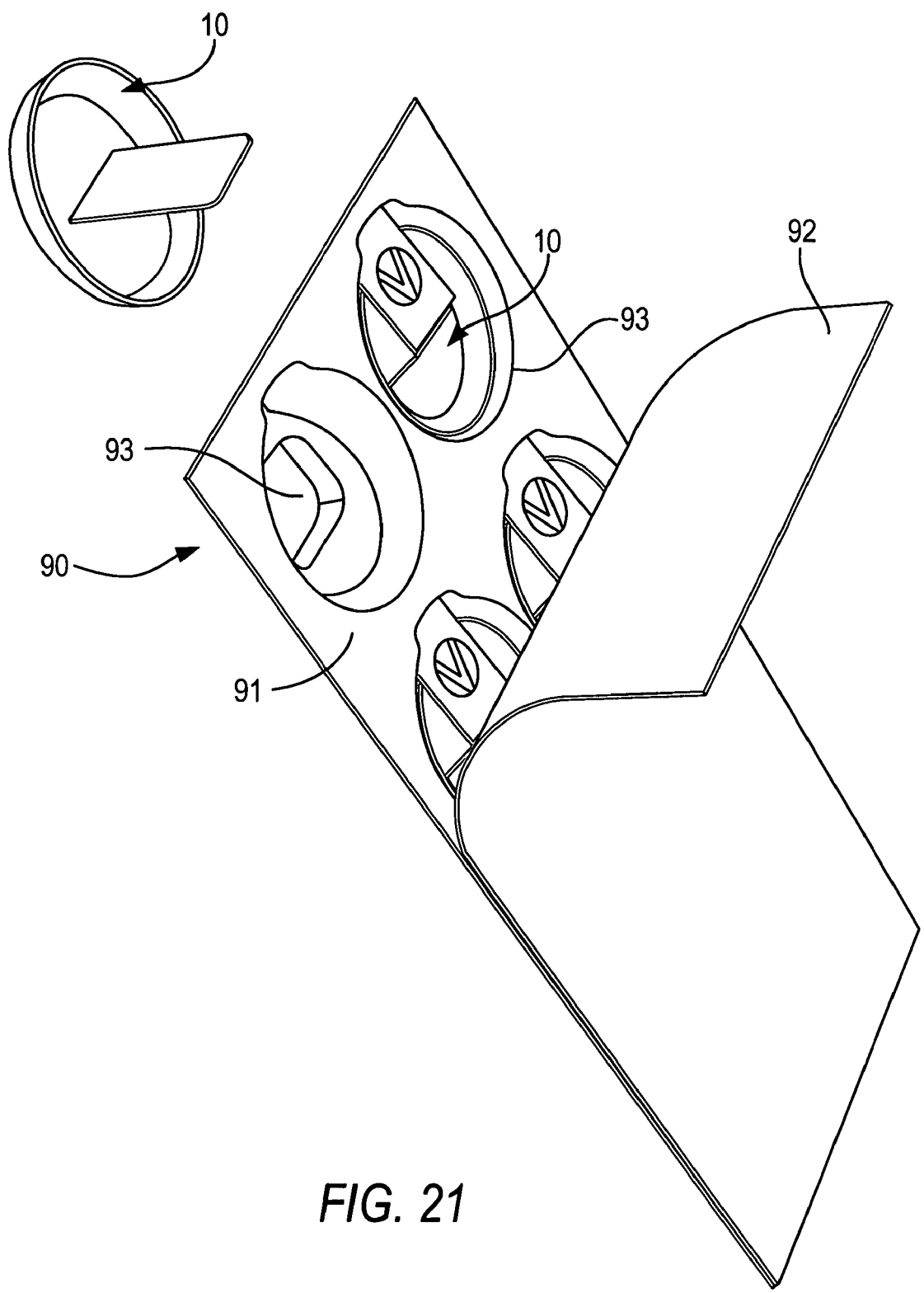
FIG. 21 shows a plurality of devices that are a variation of the fourteenth embodiment of the invention packed in a blister pack.

In an alternative arrangement, the device 10 shown in FIGS. 17-20 can be formed without any indicia and supplied with a solid unit dosage form, or tablet bonded to the surface 12. The tablet or other solid dosage form can be bonded to the surface 12 by a process involving heating one face of the tablet or other solid dosage form, to soften or melt said face, bringing said softened or melted face into contact with surface 12 and allowing the resulting assembly to cool. In an alternative embodiment, the unit dosage form or tablet can be bonded to the device 10 using an adhesive, such as a polydimethylsiloxane, collodion, a cyanoacrylate or a polymer of acrylic acid, such as a polyacrylamide or a polymethacrylate. As shown in FIG. 21, the alternative devices 10 can be supplied in blister packs 90 comprising a tray 91, formed from a thermoplastic material, and a foil cover 92. The tray 91 defines an array of individual recesses 93, each shaped to accommodate a single assembly of a device 10 and tablet. The foil cover 92 is located over the recesses 93 and a plurality of assembled devices 10 and tablets, each in a recess 93, so as to seal the assembled devices 10 and tablets in place. To gain access to a device 10 for use, the foil cover 92 can be ruptured or peeled back so as to reveal one assembly of device 10 and tablet at a time.

What follows is a detailed description of specific embodiments of the pharmaceutical compositions and formulations that can be used in conjunction with and in embodiments of the present invention as well as processes for preparing the same.

These compositions, formulations and methods of manufacture are more fully described in WO 02/00203 A1, the entire disclosure of which is hereby incorporated by reference, and below.

Pharmaceutical formulations suitable for use in connection with embodiments of the present invention may comprise a unit dose of a therapeutically effective amount of a therapeutic agent and a pharmaceutically acceptable carrier medium therefor, which is solid at ambient temperature and has a softening point of not higher than 37, 35, 34, 33 or 32° C., such that when the formulation is placed in continuous contact with the skin of a mammalian patient, it is softened to a consistency to effect substantial application of the unit dose of said therapeutic agent onto a desired skin area of the mammalian patient within a time period of less than 10, 5 or 2 minutes.

In certain embodiments of the present invention, the pharmaceutical formulation is for topical administration to a mammal, and comprises a unit dose of a therapeutically effective amount of a therapeutic agent and a pharmaceutically acceptable carrier therefor, said formulation having a softening point of not higher than skin temperature of a mammalian patient. Preferably, such formulations take the form of solid unit dosage forms that have an aspect ratio (wall:face) of less than 1:1 and can soften to a consistency to effect substantial application of the unit dose of the therapeutic agent onto a desired skin area of a mammalian patient within a time period of less than 10, 5 or 2 minutes.

The formulation preferably has a shape to facilitate the topical administration of the drug. For example, the formulation can be in the form of a tablet and can have at least one surface which is flat; at least one concave surface; at least one convex surface; two flat surfaces; two concave surfaces or two convex surfaces. The shape of the formulation can be in the form of a standard tablet, spherical or half-spherical. Bullet shaped and conical shaped formulations are not preferred in the present invention.

In preferred embodiments, the unit doses or unit dosage forms in accordance with the invention have a total weight within the range of from about 50 mg to about 1 g, preferably from about 100 mg to about 900 mg and more preferably from about 250 mg to about 750 mg. Unit doses or unit dosage forms in accordance with the invention, however, can have a weight in excess of 1 gram if desired.

Formulations and dosage forms prepared for human patients, preferably, will have a softening point not higher than the normal external temperature (skin temperature) of a human. This softening point is typically not higher than about 35° C. In certain embodiments, the formulation has a softening point within the range of about 30° C. to about 35° C.

In certain embodiments, the pharmaceutical formulation can contain a unit dose of at least one therapeutic agent suitable for topical administration to a mammalian patient. Such formulations are preferably solid during final manufacture and have, prior to application to an area of skin of said mammalian patient, a spreading consistency suitable for application to said area of skin. The formulation may be individually contained in a plastic container having a removable or breakable enclosure for dispensing said unit dose, or may be a plurality of substantially discrete substantially solid particles comprising a therapeutic agent admixed with a pharmaceutically acceptable carrier medium, e.g., in a sachet, a capsule or a device suitable to dispense a unit dose of the particles.

Solid unit dosage forms in accordance with the invention can be prepared by a tableting process. Typically, "tableting" involves introducing a flowable composition, such as a mixture of at least one therapeutic agent and a carrier medium, into a tabletting press and compressing the composition to yield a substantially solid form, typically a substantially solid dosage form or tablet.

A process for preparing a pharmaceutical formulation suitable for use in or with embodiments of the present invention can comprise cooling at least a portion of a mixture of at least one therapeutic agent and carrier medium therefor, which cooling can improve handling properties of the mixture and may also increase the speed of tabletting as carried out according to the present invention. Suitably, cooling may be carried out prior to and/or during shaping of the mixture of therapeutic agent(s) and a carrier medium. Preferably, the mixture can be cooled to a temperature of not more than about 15° C., advantageously not more than about 10° C., for example, not more than about 0° C., prior to, and/or during shaping.

The cooling may be effected at least in part by using a cooled tabletting press. Advantageously, a mixture of at least one therapeutic agent and carrier medium can also be cooled prior to being introduced into such a tabletting press.

The carrier medium may be suitable for shaping into a substantially solid dosage form at temperatures of up to about ambient or room temperature (e.g., at temperatures of up to 20, 21, 23, 24, 25, 26, 27, 28, 29, or 30° C.).

Preferably, the carrier medium constitutes not less than about 60%, more preferably not less than about 80% and even more preferably not less than about 90%, by weight based on the weight of the pharmaceutical formulation.

Any base component commonly used in suppositories can be used as or in a carrier medium or base component for the compositions and formulations employed in the practice of the present invention, including those derived from animal, vegetable or mineral origins, and materials partially or totally synthesized. Specific examples given of such base components include oils and fats of animals or vegetable origin, e.g., olive oil, corn oil, castor oil, cottonseed oil, wheat germ oil, cocoa butter, hydrogenated oils, etc.; hydrocarbons, e.g., squalane, petrolatum, solid paraffin, liquid paraffin, etc; and waxes, e.g., jojoba oil, carnauba wax, bees wax, lanolin etc. As partially or totally synthesized fatty acid esters glycerol, mono-, di-, or triglycerides of medium or higher fatty acid, such as saturated linear fatty acid, e.g., lauric acid, myristic acid, palmitic acid, stearic acid, etc., or unsaturated linear fatty acid, e.g., oleic acid, linoleic acid, linolenic acid, etc, are given. Commercial products of these base components include Witepsol (manufactured by Dynamit Nobel), Pharmasol (manufactured by Nippon Oil and Fats Co.), Isocacao (manufactured by Kao Corp.), SB (manufactured by Taiyo Oil and Fats Co.), Novata (manufactured by Henkel), Suppocire (manufactured by Gattefosse Co.), and the like. Polyethylene glycol, e.g., macrogol etc., as well as derivatives thereof, e.g., cetomacrogol, are given as examples of other synthetic products.

A first base component can be combined with another base component in order to increase or decrease the softening point to obtain a suitable product. For example, in order to decrease the softening point, a base suitable as a plasticizer can be added, e.g., glyceryl monostearate, myristyl alcohol, polysorbate 80, propylene glycol or a combination thereof. In order to increase the softening point, a base which is suitable as a hardener can be added, e.g., beeswax, cetyl alcohol, stearic acid, stearyl alcohol, aluminum monostearate, aluminum distearate, aluminum tristearate, bentonite, magnesium stearate, colloidal silicon dioxide and combinations thereof.

It is often preferred that a carrier medium employed in the pharmaceutical formulation comprises one or more glycerides, including in particular one or more glycerol esters of C8-C18 fatty acids or one or more polyglycolysed glycerides.

In certain embodiments, the carrier medium employed in the formulation consists essentially of a Witepsol grade product substantially as described above.

Alternatively, the carrier medium of the pharmaceutical formulation can comprise, or consist essentially of, a mixture of glycerides, where the glycerides can be selected from the group consisting of mono-glycerides, di-glycerides and tri-glycerides, the glycerides comprising glycerol esters of C8-C18 fatty acids or one or more polyglycolysed glycerides. Suitably such glyceride mixtures are available under the trade marks Gelucire or Suppocire and may typically be any of the following: Gelucire 33/01, Gelucire 39/01, Gelucire 43/01, Gelucire 44/14, or any of the Suppocire Standard type, Suppocire N type or Suppocire P type products.

The therapeutically and pharmaceutically active agents that can be used in the practice of the present invention include all drugs which can be delivered onto or through the skin for either a local or systemic effect. These compounds include agents in all of the major therapeutic areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, a typical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and formulation of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like.

Representative drugs include, by way of example and not for purposes of limitation, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone, dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, flucinonide, fluorometholone, flurandrenolide, halcinonide, hydrocortisone, medrysone, 6.alpha-methylprednisolone, mometasone, paramethasone, prednisolone, prednisone, tetrahydrocortisol, triamcinolone, benoxinate, benzocaine, bupivacaine, chloroprocame, cocaine, dibucaine, dyclonine, etidocaine, lidocaine, mepivacaine, pramoxine, prilocaine, procaine, proparacaine, tetracaine, alfentanil, choroform, clonidine, cyclopropane, desflurane, diethyl ether, droperidol, enflurane, etomidate, halothane, isoflurane, ketamine hydrochloride, meperidine, methohexital, methoxyflurane, morphine, propofol, sevoflurane, thiamylal, thiopental, acetaminophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sufasalazine, sulindac, tolmetin, acetophenazine, chlorpromazine, fluphenazine, mesoridazine, perphenazine, thioridazine, trifluorperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, dezocine, diphenoxylate, drocode, hydrocodone, hydromorphone, levallorphan, loperamide, meptazinol, methadone, naibuphine, nalmefene, nalorphine, naloxone, naltrexone, oxybutynin, pentazocine, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin and flufenamic acid.

Other representative drugs include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscanmc agent such as anisotropine, atropine, clidinium, cyclopentolate, dicylcomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17.beta.estradiol (or estradiol), semi-synthetic estrogen derivatives such as the esters of natural estrogen, such as estradiol-17.beta.enanthate, estradiol-17.beta.-valerate, estradiol-3-benzoate, estradiol-17.beta.-undecenoate, estradiol 16,17-hemisuccinate or estradiol-17.beta.-cypionate, and the 17-alkylated estrogens, such as ethinyl estradiol, ethinyl estradiol-3-isopropylsulphonate, and the like, an androgen such as danazol, fluoxymesterone, methandrostenolone, methyltestosterone, nandrolone deconoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like; cannebidiol; and 4-hydroxy quinolone derivatives (e.g., chloroquine, hydroxychloroquine).

In embodiments where the-active drugs produce a local effect, the agents include, but are not limited to (in addition to local agents listed above), antiviral agents (e.g., acyclovir and idoxuridine, etc.), antifungal agents (e.g., amphotericin B, clotrimazole, nystatin, ketoconazole, miconazole, butocouazole, haloprogin, etc.), antibiotic agents (penicillins, cephalosporins, erythromycin, tetracycline, clindamycin, aminoglycosides, chloramphenicol, polymixin b, bacitracin, neomycin, gentamycin etc.), antiseptics (e.g., povidone-iodine, methylbenzethonium chloride, etc.), antiparasitics (e.g., lindane, anthralin, etc.), analgesic agents (e.g., methylsalicylate, salicylic acid, dyclonine, aloe vera etc.), local anesthetics (e.g., benzocalne, lidocaine, xylocaine, butamben picrate, etc.), anti-inflammatory agents (e.g., steroidal compounds such as dexamethasone, betamethasone, prednisone, predinisolone, triamcinolone, hydrocortisone, alclometasone, amcinonide, diflorasone, etc., as well as non-steroidal anti-inflammatories), anti-itch and irritation-reducing compounds (e.g., antihistamines such as diphenhydramine and psoriasis treatments); burn relief compounds (e.g., o-amino-p-toluenesulfonamide, monoacetate, etc.); depigmenting agents (e.g., monobenzone); and hormonal agents (e.g., oestriol).

The compounds that can be used in the unit dose, including the compounds listed above, are meant to include all pharmaceutically acceptable salts and conjugates.

Other topically-active compounds are listed in Remington's Pharmaceutical Sciences, $17^{th}$ Ed., Merck Publishing Co., Easton, Pa. (1985), pages 773-791 and pages 1054-1058 (hereinafter Remington's), incorporated herein by reference.

The spreadable composition can be prepared for other applications, such as for cosmetic purposes, e.g., antiperspirants, sunblocks, keratolitics, skin softeners, fragrances and anti-acne preparations.

It will be understood that where the therapeutic agent is for treatment of a local condition of the skin, substantial absorption by at least the outer epidermal layers of the skin of the patient will suffice for treatment of the patient and substantial transdermal passage into the bloodstream is not required and indeed in some instances will not be desirable.

It may be advantageous to employ in a pharmaceutical formulation, one or more tableting aids, which may, for example, be selected from antiadhesives (for example, talc or the like); flow aids (for example, silicon dioxide or the like); and compaction aids (for example, microcrystalline cellulose, dicalcium phosphate or the like) or any other ingredient suitable for use as a tableting aid in formulations and processes for manufacturing the same.

The terms "therapeutic agent", "pharmaceutically active agent" and the like as used herein denote any active substance suitable for dermal administration to a patient (particularly a human patient) in any composition, formulation or product in accordance with the present invention. It is preferred that the therapeutic or pharmaceutically active agent is suitable for topical application to the skin, but it can be a systemically active agent that is absorbed through the skin. Such agents include all of the drugs and classes of drugs referred to in foregoing passages, plus pharmaceutically acceptable equivalents thereof, such as their pharmaceutically acceptable salts, esters, prodrugs and active metabolites. Isomers of all disclosed agents are also encompassed by this disclosure.

The terms "dermally administered" or "dermal administration" are used herein to include (i) administration of a therapeutic agent suitable for local or topical treatment of a disorder of the skin and (ii) administration of a therapeutic agent suitable for non-local treatment, in other words for administration into the blood stream of a patient particularly a human patient) as a systemic treatment.

The term "treatment" as used herein includes the treatment of established conditions as well as the prophylaxis thereof. The precise manner in which any pharmaceutical composition, formulation, product or method according to the present invention should be used will of course depend on the precise nature of a condition being treated, the age and sex of the patient and will ultimately be at the discretion of an attendant physician.

The term "spreading point" as used herein refers to a temperature at which the formulation has a "spreading" consistency, for example, the formulation may flow under its own weight or at least can be spread upon the skin of a human or animal patient, for example, using finger pressure. That mobility of a formulation having a spreading consistency may promote the absorption of a therapeutic agent into the skin by allowing movement of the therapeutic agent towards the skin, for example, by diffusion. The spreading point of a preparation may be measured using the TA-XT2 texture analyser mentioned above in relation to measurement of softening point and with this analyser the spreading point of a formulation is the temperature at which outward flow of the formulation is first observed on advance of the flat faced probe into the preparation.

The term "unit dose" means a discrete aliquot of a composition or formulation that is suitable for administration in one single application and preferably contains an effective amount of an agent to be administered, for example, a therapeutically active agent or a cosmetic agent.

Therapeutic agents employed in the unit doses described herein should be present in a therapeutically effective concentration, for example, at least 0.01% by weight based on the total weight of the pharmaceutical formulation. In general, the therapeutic agent will be present in an amount of not more than 10%, advantageously, not more than 5% more advantageously not more than 2% preferably not more than 1%, more preferably not more than 0.05%, by weight based on the total weight of the pharmaceutical formulation.

Exemplary unit doses suitable for use in and with embodiments of the present invention are set forth in the following examples, which do not limit the invention in any way:

Example 1

| Tablet Ingredients: | |
| --- | --- |
| Lignocacine | 2% |
| Tween 62 (Emulsifier) | 5% |
| 30 Witepsol S55* | 93% |

*A low melting (33° C. to 35° C.) triglyceride

Percentages are by weight based on the total weight of the combined ingredients.

Method of Preparation:

The ingredients were mixed for 5 minutes in a high shear mixer blender, to form a granular mixture. The mixture was cooled by immersion in dry ice contained in a receptacle. The tablets were then compressed on a Manesty F press using 10 mm flat faced zirconia tooling. The mixture was compacted under the compression and then solidified to form a tablet.

Example 2

| Tablet Ingredients (per tablet): | |
| --- | --- |
| Hydrocortisone | 0.005 g |
| Cocoa Butter | 0.275 g |

Method of Preparation:

Cocoa Butter was gently melted down until molten and homogenous. Hydrocortisone was then added and was mixed in whilst gently heating. The mixture was cooled and then left in the fridge overnight to harden. Once hard the solid was then broken and granulated. Tablets were compressed on a Riva Picolla ten station tablet press using 10 mm flat faced stainless steel/Zirconia tooling. The mixture was compacted under the compression and then solidified to form tablets.

Example 3

| Tablet Ingredients (per tablet): | |
| --- | --- |
| Hydrocortisone | 0.005 g |
| Witepsol H15 | 0.334 g |

Method of Preparation:

Witepsol H15 was gently melted down until molten and homogenous. Hydrocortisone was then added and was mixed in whilst gently heating. The mixture was cooled and then left in a fridge overnight to harden. Once hard the solid was then broken down and granulated. The granulate was compressed into tablets on a Riva Picolla ten station tablet press using 10 mm flat faced stainless steel/Zirconia tooling. The mixture was compacted under the compression and then solidified to form a tablet.

Example 4

| Dosage Ingredients: | |
| --- | --- |
| Hydrocortisone | 1% |
| Carrier | 99% |

Four different carrier formulations were used in dosages prepared according to Example 4 as follows:

| Formulation 1: | |
| --- | --- |
| Castor Oil | 50% |
| Cocoa Butter | 50% |
| Formulation 2: | |
| Castor Oil | 60% |
| Cocoa Butter | 40% |

-continued

| Formulation 3: | |
|---|---|
| Castor Oil | 70% |
| Cocoa Butter | 30% |
| Formulation 4: | |
| Almond Oil | 70% |
| Cocoa Butter | 30% |

Method of Preparation:

Cocoa Butter and the selected oil were gently melted down until molten and homogenous. Hydrocortisone was then added and was mixed in whilst gently heating. The mixture was cooled, the left in the freezer to harden. Once hard the solid was broken down and the granulated at a low temperature. The dosages were prepared by compressing on a Riva Picolla ten station tablet press using 10 mm flat faced stainless steel/Zirconia tooling. The mixture was compacted under the compression at a temperature of 0 to −4° C. and solidified to form solid dosages which were allowed to reach room temperature and subsequently soften.

Example 5

| Formulation 5a (ingredients) | |
|---|---|
| Softisan 133 (Hydrogenated coco-glycerides) | 59.5% (w/w) |
| Softisan 378 (Caprylic/Capric/Myristic/Stearic Triglyceride) | 39.5% (w/w) |
| Corticosteroid | 1% |
| Formulation 5b (ingredients) | |
| Dry Flo AF Pure (Corn Starch modified) | 5% (w/w) |
| Myristic acid Isopropyl ester | 5% (w/w) |
| Witepsol S51 | 89% (w/w) |
| Corticosteroid | 1% |

Method of Manufacture

Base materials are melted down until molten and homogenous. The drug (corticosteroid) is added to the molten mixture and is mixed until homogenous. The mixture is solidified by cooling. The solid bulk is broken down by low temperature milling and is granulated to control the particle size. The granulate is compressed into tablet form using a Riva Picolla ten station tablet press using 10 mm flat faced stainless steel/Zirconia tooling.

Example 6

Figure 22:
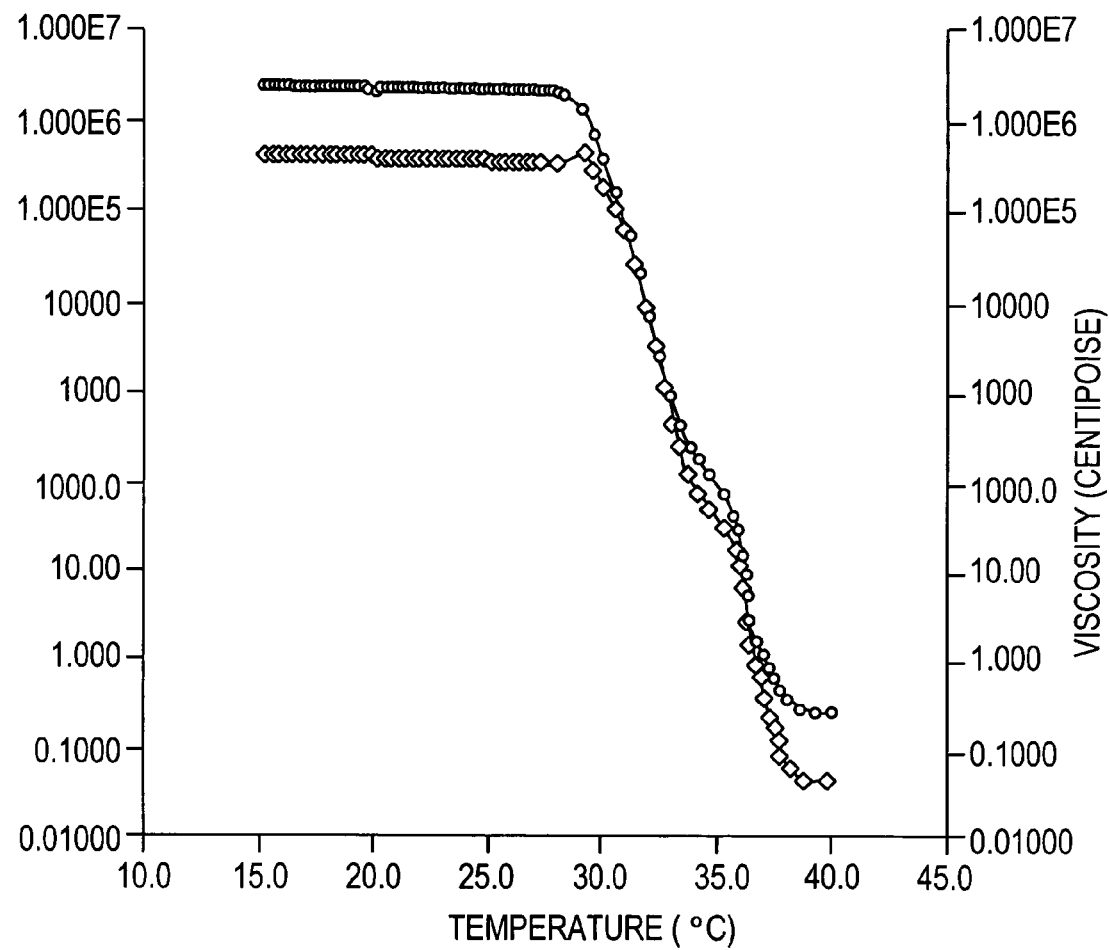
FIG. 22 shows the change in viscosity with increasing temperature of two spreadable compositions in accordance with the invention.

The change in viscosity with temperature of two spreadable compositions in accordance with the invention was measured using an AR500 Rheometer, manufactured by TA Instruments Ltd, Cleeve Road, Leatherhead, Surrey KT22 7UQ, United Kingdom. Viscosity measurements were taken as the tested samples were heated from 15.0° C. to 40.0° C. at a rate of 1.0° C. per minute and the results are set out in FIG. 22.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

The invention claimed is:

1. A non-adhesive applicator for applying a spreadable pharmaceutical composition to the skin or other exterior region of a human or animal body, comprising
   a receiving member for receiving and carrying a unit dose of the pharmaceutical composition; and
   a grip for enabling a user to grip and manipulate the applicator;
   wherein the receiving member has a recess, and the grip and receiving member are arranged such that a user gripping the applicator by the grip is protected from inadvertent contact with the pharmaceutical composition, a unit dose of which is carried by and coupled to the receiving member to provide a face exposed for application to said skin or other exterior region, and at least a portion of the unit dose is accommodated within the recess, wherein the composition remains solid when heated to temperatures of up to 28° C., but softens sufficiently to be spreadable, or has a softening point, when heated to a temperature no higher than 37° C. and so softens on contact with the skin of a live human or animal body, thereby allowing it to be spread, and wherein substantially all of the unit dose accommodated in the recess may be applied through skin contact induced erosion at said exposed face of the unit dose;
   wherein the applicator is of non-absorptive material and wherein the applicator includes a flexible flange which prevents contact between the unit dose and the user and enables the applicator to be pushed down onto the skin in a closed environment, said flexible flange extending from the receiving member and having a free end which does not contact the grip of the applicator.

2. An applicator as claimed in claim 1, shaped to shield the grip, or a zone in the vicinity of the grip, from contact with a composition, a unit dose of which is carried by the receiving member.

3. An applicator as claimed in claim 1, comprising a shroud around at least a portion of the grip, or a zone in the vicinity of the grip, wherein the shroud is arranged to shield said zone or portion of the grip from a composition, a unit dose of which is carried by the receiving member.

4. An applicator as claimed in claim 1, wherein the grip is arranged to be held between a finger and thumb of a user's hand.

5. An applicator as claimed in claim 4, shaped to shroud the tips of a finger and thumb holding the grip.

6. An applicator as claimed in claim 1, wherein the grip is in the form of a sheath arranged to engage and accommodate a user's finger or thumb.

7. An applicator as claimed in claim 1, wherein the receiving member forms a portion of a spreading means for facilitating the spreading of a composition, a unit dose of which is carried by the receiving member, on the skin or other exterior region of a human or animal body.

8. An applicator as claimed in claim 7, wherein the receiving and spreading members are integrally formed.

9. An applicator as claimed in claim 7, comprising a combined spreading and receiving member, wherein said combined spreading and receiving member also serves to shield the grip, or a zone in the vicinity of the grip, from contact with a composition, a unit dose of which is carried by the receiving member.

10. An applicator as claimed in claim 1 in the form of a single piece moulding.

11. An applicator as claimed in claim 1, wherein the grip is foldable or collapsible from a position where is it extended for use into a storage position.

12. An applicator as claimed in claim 11, further comprising means for releasably retaining the grip in said storage position.

13. An applicator as claimed in claim 1, wherein the recess is configured to confine at least an uneroded portion of the unit dose.

14. An applicator as claimed in claim 13, wherein the recess is configured to resist displacement of said portion of the unit dose from the recess other than as a result of skin contact induced erosion at said exposed face of said the unit dose.

15. An applicator as claimed in claim 1, wherein a first recess defining portion of the receiving means is resiliently mounted with respect to a second recess defining portion of the receiving means to provide said automatic depth adjustment.

16. An applicator as claimed in claim 1, wherein the first and second recess defining portions of the receiving means form a platform, a first portion of which is recessable relative to a second to provide said recess.

17. An applicator as claimed in claim 16, wherein the first portion of the platform is surrounded by the second portion of the platform.

18. An applicator as claimed in claim 16, wherein the first portion of the platform is variably recessable relative to the second.

19. An applicator as claimed in claim 16, wherein the first recess defining portion of the receiving means is embodied by the first portion of the platform and the second recess defining portion of the receiving means is embodied by the second portion of the platform.

20. An applicator as claimed in claim 16, wherein the first portion of the platform comprises a pad in a fixed relationship with the grip, said pad being surrounded by the second portion of the platform, and said second portion of the platform is retractable relative to the pad and grip against resilient pressure.

21. An applicator as claimed in claim 1, wherein the first and/or second portion(s) of the platform is or are resiliently mounted.

22. An applicator as claimed in claim 1, wherein the first recess defining portion of the receiving means is embodied by the second portion of the platform and the second recess defining portion of the receiving means is embodied by the first portion of the platform.

23. An applicator as claimed in claim 1, wherein the grip, or a zone in the vicinity of the grip, is protected or shielded from contact with the spreadable composition during application of the latter.

24. An applicator as claimed in claim 1, wherein the solid unit dosage form is a solid tablet.

25. An applicator as claimed in claim 1, wherein the softening point of the solid composition or unit dosage form is the temperature at which its viscosity is reduced to 100,000 centipoise, or below.

26. An applicator as claimed in claim 25, wherein the softening point of the solid composition or unit dosage form is the temperature at which its viscosity is reduced to 50,000 centipoise, or below.

27. An applicator as claimed in claim 1, wherein the solid composition or unit dosage form becomes substantially liquid when heated to a physiological temperature, or to a temperature of at least 33° C.

28. An applicator as claimed in claim 1, wherein, when placed in continuous contact with the skin of a living human or animal body, the solid unit dosage form will soften to a consistency to effect substantial application of the unit dosage form onto the contacted skin within a time period of less than 10 minutes.

29. An applicator as claimed in claim 1, wherein the pharmaceutical composition or formulation comprises a unit dose of a pharmaceutically active agent and a pharmaceutically acceptable carrier.

30. An applicator as claimed in claim 29, wherein when placed in continuous contact with the skin of a living human or animal body the pharmaceutical composition or formulation will soften to a consistency to effect substantial application of the unit dose of said pharmaceutically active agent onto the contacted skin within a time period of less than 10 minutes.

31. An applicator as claimed in claim 1 packaged in a sealed container.

32. An applicator as claimed in claim 31, wherein said applicator is one of a plurality of applicators, each packaged in one of a plurality of sealed containers and said containers form part of an array of such containers.

33. A method of treating a human or animal body, comprising applying a spreadable composition to the skin or other external part of said body with an applicator as claimed in claim 1.

34. A kit comprising an applicator as claimed in claim 1 and at least one separately packaged unit dosage form.

35. A kit as claimed in claim 34, wherein said unit dosage form is a solid tablet.

36. A method of coupling a solid unit dosage form to an applicator as claimed in claim 1, comprising heating and melting or softening a surface of the dosage from, contacting that surface with the receiving means and cooling the resulting assembly to harden the melted or softened portion of the dosage form and cause it to become bonded to the receiving means.

37. An applicator as claimed in claim 1 including a surface having indicia of measurement thereon, the surface configured to receive a measured dosage of a pharmaceutical formulation in extruded form.

38. A non-adhesive device for topically treating a desired skin region of a living being, the device comprising:
  a unit dose of a pharmaceutical formulation including a therapeutically effective amount of a therapeutic agent and a pharmaceutically acceptable carrier medium therefore, carried by and coupled to a receiving member to provide a face exposed for application to said skin or other exterior region; wherein the receiving member has a recess and wherein at least a portion of the unit dose is accommodated within the recess;
  the formulation being solid at ambient temperature and having a softening point of not higher than 35° C., such that when the formulation is placed in a continuous contact with the desired skin region, said formulation is softened to a consistency to effect substantial application of the unit dose onto the desired skin region within a time period of less than 10 minutes, and wherein substantially all of the unit dose accommodated in the recess may be applied through skin contact induced erosion at said exposed face of the unit dose; and
  an applicator member having a first portion coupled to the unit dose and a second portion configured for being held by a user;
  wherein the applicator member is of non-absorptive material and wherein the applicator member includes a flexible flange between the first and second portions which prevents contact between the unit dose and the user and enables the applicator to be pushed down onto the skin in a closed environment, said flexible flange extending from the first portion and having a free end which does not contact the second portion of the applicator.

39. A device as claimed in claim 38, wherein the user is the living being.

40. A device as claimed in claim 39, further comprising an intermediate member attached to the unit dose, and wherein the first portion of the applicator member is configured to be removably attachable to the intermediate member.

41. A device as claimed in claim 39, wherein the first portion of the applicator is removably attachable to the unit dose.

42. A device as claimed in claim 39, wherein the second portion includes a hollow cylindrical portion configured to surround a fingertip of the user.

43. A device as claimed in claim 39, further comprising a protective wrapper surrounding the applicator and unit dose and sealing the unit dose from an outside environment.

44. A device as claimed in claim 38, wherein the user is a second living being.

45. A device as claimed in claim 38, wherein the unit dose is tablet-shaped.

46. A device as claimed in claim 38, wherein the unit dose has an aspect ratio (wall:face) of less than 1:1.

47. A device as claimed in claim 38, further comprising a protective layer adhering to the applicator and sealing the unit dose from an outside environment.

48. A device as claimed in claim 38, wherein the applicator includes a flange between the first and second portions.

49. A device as claimed in claim 38, wherein the second portion includes an elongated tab configured to be gripped by the user.

50. A device as claimed in claim 38, further comprising a protective shield removably attached to the applicator and configured to protect the unit dose from an outside atmosphere.

51. A device as claimed in claim 50, wherein the protective shield is configured to be attachable to the second portion of the applicator so as to aid the user in holding the applicator.

52. A device as claimed in claim 38, wherein the pharmaceutical formulation has a softening point of not higher than the skin temperature of the desired skin region.

53. A device as claimed in claim 38, wherein the pharmaceutical formulation, upon being placed into continuous contact with the desired skin region, is softened to a consistency to effect substantial application of the unit dose within a time period of less than 10 minutes.

54. A device as claimed in claim 38, wherein the living being is a mammalian patient.

55. A device as claimed in claim 38, wherein the mammalian patient is a human.

56. A non-adhesive applicator for applying a spreadable pharmaceutical composition to the skin or other exterior region of a human or animal body, comprising
    a receiving member for receiving and carrying a unit dose of the pharmaceutical composition; and
    a grip for enabling a user to grip and manipulate the applicator, said grip extending from the receiving member;
    wherein the receiving member has a recess, and the grip and receiving member are arranged such that a user gripping the applicator by the grip is protected from inadvertent contact with the pharmaceutical composition, a unit dose of which is carried by and coupled to the receiving member to provide a face exposed for application to said skin or other exterior region, and at least a portion of the unit dose is accommodated within the recess, wherein the composition remains solid when heated to temperatures of up to 28° C., but softens sufficiently to be spreadable, or has a softening point, when heated to a temperature no higher than 37° C. and so softens on contact with the skin of a live human or animal body, thereby allowing it to be spread, and wherein substantially all of the unit dose accommodated in the recess may be applied through skin contact induced erosion at said exposed face of the unit dose;
    wherein the applicator is of non-absorptive material and wherein the applicator includes a flexible flange which prevents contact between the unit dose and the user and enables the applicator to be pushed down onto the skin in a closed environment, said flexible flange extending from the receiving member and having a free end which does not contact the grip of the applicator.

57. A non-adhesive device for topically treating a desired skin region of a living being, the device comprising:
    a unit dose of a pharmaceutical formulation including a therapeutically effective amount of a therapeutic agent and a pharmaceutically acceptable carrier medium therefore, carried by and coupled to a receiving member to provide a face exposed for application to said skin or other exterior region; wherein the receiving member has a recess and wherein at least a portion of the unit dose is accommodated within the recess;
    the formulation being solid at ambient temperature and having a softening point of not higher than 35° C., such that when the formulation is placed in a continuous contact with the desired skin region, said formulation is softened to a consistency to effect substantial application of the unit dose onto the desired skin region within a time period of less than 10 minutes, and wherein substantially all of the unit dose accommodated in the recess may be applied through skin contact induced erosion at said exposed face of the unit dose; and
    an applicator member having a first portion coupled to the unit dose and a second portion extending from said first portion configured for being held by a user;
wherein the applicator member is of non-absorptive material and wherein the applicator includes a flexible flange which prevents contact between the unit dose and the user and enables the applicator to be pushed down onto the skin in a closed environment, said flexible flange extending from the first portion and having a free end which does not contact the second portion of the applicator.

* * * * *